United States Patent
Beke et al.

(10) Patent No.: US 10,329,296 B2
(45) Date of Patent: Jun. 25, 2019

(54) INDOLE DERIVATIVES

(71) Applicant: Richter Gedeon Nyrt., Budapest (HU)

(72) Inventors: Gyula Beke, Budakeszi (HU); János Éles, Budapest (HU); András Boros, Veresegyház (HU); Sándor Farkas, Budapest (HU); György Miklós Keserü, Budapest (HU)

(73) Assignee: Richter Gedeon NYRT., Budapest (HU)

( * ) Notice: Subject to any disclaimer, the term of this patent is extended or adjusted under 35 U.S.C. 154(b) by 0 days.

(21) Appl. No.: 15/563,259

(22) PCT Filed: Apr. 14, 2016

(86) PCT No.: PCT/IB2016/052110
§ 371 (c)(1),
(2) Date: Sep. 29, 2017

(87) PCT Pub. No.: WO2016/166684
PCT Pub. Date: Oct. 20, 2016

(65) Prior Publication Data
US 2018/0093989 A1    Apr. 5, 2018

(30) Foreign Application Priority Data
Apr. 15, 2015  (HU) .................... 1500169

(51) Int. Cl.
| | | |
|---|---|---|
| A61K 31/551 | (2006.01) |
| C07D 487/04 | (2006.01) |
| A61P 3/00 | (2006.01) |
| A61P 25/00 | (2006.01) |

(52) U.S. Cl.
CPC ................. C07D 487/04 (2013.01)

(58) Field of Classification Search
CPC ............................ A61K 31/551; C07D 487/04
See application file for complete search history.

(56) References Cited

U.S. PATENT DOCUMENTS

| | | |
|---|---|---|
| 2011/0003793 A1 | 1/2011 | Guzzo et al. |
| 2014/0206696 A1 | 7/2014 | Guzzo et al. |

FOREIGN PATENT DOCUMENTS

| | | |
|---|---|---|
| EP | 1916239 | 4/2008 |
| WO | WO 01/72752 | 10/2001 |
| WO | WO 2005/019240 | 3/2005 |
| WO | WO 2008/134480 | 11/2008 |
| WO | WO 2008/140239 | 11/2008 |
| WO | WO 2009/009501 | 1/2009 |
| WO | WO 2009/089482 | 7/2009 |
| WO | WO 2010/125390 | 11/2010 |
| WO | WO 2010/141539 | 12/2010 |
| WO | WO 2011/127643 | 10/2011 |
| WO | WO 2013/131935 | 9/2013 |
| WO | WO 2013/149362 | 10/2013 |
| WO | WO 2014/039411 | 3/2014 |

OTHER PUBLICATIONS

Kawauchi, H., et al., "Characterization of melanin-concentrating hormone in chum salmon pituitaries," *Nature* 305:321-323, 1983, Macmillan Journal Ltd.
Qu, D., et al., "A role for melanin-concentrating hormone in the central regulation of feeding behavior," *Nature* 380:243-247, 1996, Nature Publishing Group.
Rossi, M., et al., "Melanin-concentrating hormone acutely stimulates feeding, but chronic administration has no effect on body weight," *Endocrinology* 138:351-355, 1997, The Endocrinology Society.
Shimada, M., et al., "Mice lacking melanin-concentrating hormone are hypophagic and lean," *Nature* 396:670-674, 1998, Macmillan Publishers.
Hervieu, G.J., et al., "The distribution of the mRNA and protein products of the melanin-concentrating hormone (MCH) receptor gene, slc-l., in the central nervous system of the rat," *Eur. J. Neurosci.* 12:1194-1216, 2000, European Neuroscience Association.
Saito, Y., et al., "Expression of the melanin-concentrating hormone (MCH) receptor mRNA in the rat brain," *J. Compar. Neurol.* 435:26-40, 2001, Wiley-Liss, Inc.
Borowsky, B., et al., "Antidepressant, anxiolytic and anorectic effects of a melanin-concentrating hormone-1 receptor antagonist," *Nature Med.* 8:825-830, 2002, Publishing Group.
Pissios, P., et al., "Melanin-concentrating hormone: from fish skin to skinny mammals," *Trends Endocrin. Metabol.* 14:243-248, 2003, Elsevier.
Pissios, P., "Animal models of MCH function and what they can tell us about its role in energy balance," *Pepticies*,30:2040-2044, 2009, Elsevier.
Gomori, A., et al., "Chronic intracerebroventricular infusion of MCH causes obesity in mice," *Am. J. Physiol. Endocrinol. Metab.* 284:E583-E588, 2003, American Physiological Society.

(Continued)

*Primary Examiner* — Brenda L Coleman
(74) *Attorney, Agent, or Firm* — Sterne, Kessler, Goldstein & Fox P.L.L.C.

(57) ABSTRACT

The present invention relates to compounds of the general form (I). The present invention relates to new substituted diazepino-indole derivatives of the general formula (I), and to pharmaceutically acceptable salts thereof, as well as to pharmaceutical compositions comprising such compounds, to new intermediate thereof, as well as to the use of such compounds in treatment or prevention of disorders associated with melanin-concentrating hormone receptor 1 activity.

(I)

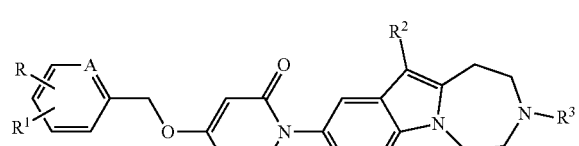

21 Claims, No Drawings

(56) References Cited

OTHER PUBLICATIONS

Ludwig, D.S., et al., "Melanin-concentrating hormone overexpression in trasgenic mice leads too obesity an dinsulin resistance," *J. Clin. Invest.* 107:379-386, 2001, American Society for Clinical Investigation.

Ito, M., et al., "Mechanism of the anti-obesity effects induced by a novel melanin-concentrating hormone l-receptor antagonist in mice," *Eur. J. Pharmacol.* 624:77-83, 2009, British Pharmacological Society.

Smith, D.G., et al., "Melanin-concentrating hormone-I receptor modulates neuroendocrine, behavioral, and corticolimbic neurochemical stress responses in mice," *Neuropsychopharmacol.* 31:1135-1145, 2006, Nature Publishing Group.

David, D.J., et al., "Efficacy of the MCHR1 Antagonist N-[3-(1-{[4-(3,4-difluorophenoxy)phenyl]methyl}(4-piperidyl))-4-methylphenyl]-2-methylpropanamide (SNAP 94847) in mouse models of anxiety and depression following acute and chronic administration is independent of hippocampal neurogenesis," *J. Pharmacol. Exper. Therap.* 321:237-248, 2007, The American Society for Pharmacology and Experimental Therapeutics.

Gehlert, D.R., et al., "Preclinical evaluation of melanin-concentrating hormone receptor 1 antagonism for the treatment of obesity and depression," *J. Pharmacol. Exper. Therap.* 329:429-438, 2009, Experimental Therapeutics.

Kokkotou, E., et al., "Melanin-concentrating hormone as a mediator of intestinal inflammation," *PNAS* 105:10613-10618, 2008, The National Academy of Sciences of the USA.

Fitpatrick, L.R., et al., "Melanin-concentrating hormone receptor I antagonists attenuate TNBS-induced colitis in mice," *AGA Abstracts, Gastroenterol.* 136:A-403, 2009, Elsevier.

Ziogas, D.C., et al., "Anti-melanin-concentrating hormone treatment attenuates chronic experimental colitis and fibrosis," *Am. J. Physiol. Gastrointest. Liver Physiol.* 304:G876-G884, 2013, The American Physiological Society.

Kokkotou, E., et al., "Melanin-concentrating hormone (MCH) modulates *C difficile* toxin A-mediated enteritis in mice," *Gut* 58:34-40, 2009, BMJ Group.

Ennis, M.D., etal., "2,3,4,5-tetrahydro- and 2,3,4,5,11,11a-hexahydro-1H-[1,4]diazepino[1,7-α]indoles: new templates for 5-$HT_{2C}$ agonists," *Bioorgan. Med. Chem. Letters* 13:2369-2372, 2003, Pergamon.

INDOLE DERIVATIVES

FIELD OF THE INVENTION

The present invention relates to new substituted diazepino-indole derivatives of the general formula (I), and to pharmaceutically acceptable salts thereof, as well as to pharmaceutical compositions comprising such compounds, to new intermediate thereof, as well as to the use of such compounds in treatment or prevention of disorders associated with melanin-concentrating hormone receptor 1 activity.

BACKGROUND OF THE INVENTION

Melanin-concentrating hormone (MCH), a cyclic neuropeptide, consist of 19 amino acids, which was originally described in salmon pituitary and isolated from its extract (Kawauchi et al., Nature 305: 321-323 (1983)). Later MCH was identified in mammals also as a cyclic nonadeca peptide.

The first MCH receptor (which was called later MCHR1), a G-protein coupled receptor (GPCR), was identified with "reverse pharmacological" approach, namely it was shown, that in mammals MCH is the natural ligand of orphan GPCR (SLC1). Thereafter a second MCH receptor (MCHR2) was also identified. In human both receptor sub-type can be found, while in rodents only MCHR1.

The melanin-concentrating hormone receptor 1 (MCHR1) plays an important role in the regulation of the energy homeostasis, food intake, reward as well as the nutrition behaviour. The role of MCH in the energy homeostasis and food intake of mammals has long been studied (Qu et al., Nature 380: 243-247 (1996); Rossi et al., Endocrinology 138: 351-355 (1997); Shimada et al., Nature 396: 670-674 (1998)).

The neurons, producing the melanin-concentrating hormone (MCH), can be found in the tuberal region of hypotalamus, which is the integrating center of the neurohumoral regulation of the energy homeostasis and stress reactions. MCHR1 can be found in many regions of the brain and is distributed mainly in areas implicated in the regulation of nutrition, energy balance, emotion and stress. (Hervieu et al., Eur J Neurosci 12: 1194-16 (2000), Saito et al., J Comp Neurol 435: 36-40 (2001), Borowsky et al., Nat Med 8: 825-30 (2002)). The MCH is expressed mainly in the lateral hypothalamic area as well as in the subthalamic zona incerta.

In rodents the MCH simultaneously stimulates food intake as well as energy balance. (Pissios and Maratos-Flier, Trends Endocrinol Metabol 14: 243-48 (2003); Pissios et al., Peptides 30: 2040-44 (2009)). MCH expression is increased in fasted animals and in leptin-deficient ob/ob mice. Upon acute icy administration of MCH food intake substantially increased and catabolic activity decreased. (Qu et al., Nature 380: 243-47 (1996)). Cronic icy administration of MCH results in an encreased calorie uptake and a significant increase in bodyweight. Furthermore the treated animals showed—similarly to the human metabolic symptoms—an increased glucose, insulin and leptin level (Gomori et al., Am J Physiol Endocrinol Metab 284: E583-88 (2003)).

In line with this elimination of the MCH gen (KO) makes the mice resistant to diet-induced obesity (DIO=diet-induced obesity). Transgenic mice overexpressing the MCH gen consumed 10% more calories and gained 12% more weight than controls on high fat diet. High blood glucose and insulin-resistance also appeared, consistent with a pre-diabetic state (Ludwig et al., J. Clin. Invest. 107, 379-386 (2001)). The MCHR1 KO mice, exhibited slightly increased food intake, but are resistant to diet-induced obesity and their metabolism is increased (Shimada et al.: Nature 396: 670-674 (1998)).

Rodents treated with MCHR1 antagonist showed a decreased food intake and better metabolic condition, especially when they were placed on a high-fat diet (Pissios et al., Peptides 30: 2040-44 (2009); Ito et al., Eur J Pharmacol 624: 77-83 (2009)).

MCHR1 antagonists may play a role not only in the regulation of body weight, but also in the treatment of anxiety and depression (Smith et al., Neuropsychopharmacol 31: 1135-45 (2006); David et al., J Pharmacol Exp Ther 321: 237-48 (2007); Gehlert et al., J Pharmacol Exp Ther 329:429-38 (2009)).

The MCHR1 is also involved in the patogenesis of the experimentalcolitis which is considered to be the relevant modell of the human inflammatory bowel disease (e.g. Crohn disease). The systemic application of MCHR1 antibody or MCHR1 antagonist to rodents decreased the severity of the experimentally induced acut inflammation of the colon and increased the rate of recovery (Kokkotou et al., Proc Natl Acad Sci USA 105: 10613-18 (2008); Fitzpatrik et al., AGA Abstracts, Gastroenterology 136 (5 supl 1)A-403 (2009); Ziogas et al., Am J Physiol Gastrointest Liver Physiol 304: G876-84 (2013)).

The MCHR1 plays also a role in the development of acut intestinal inflammation which was proved in mice treated with *C. difficile* A toxin (Kokkotou et al., Gut 58: 34-40 (2009)).

Antagonization of MCHR1 with low molecular weight substances is considered to be a promising strategy for the treatment of obesity, depression, anxiety and inflammatory bowel diseases. The following patent applications deal with MCH receptor antagonists: Tempest et al. WO2005/019240, Washburn et al. WO2008/134480; Suh et al. WO2008/140239; Stein et al. WO2009/009501; Johansson et al. WO2010/125390; Christensen et al. WO2010/141539; Lin et al. WO2011/127643; Oost et al. WO2013/131935; Qin et al. WO2013/149362; Ahmad et al. WO2014/039411.

Since the discovery of the MCH receptors a large number of compounds with antagonistic activity were described. Despite several clinical investigations none of the compounds reached the therapeutic application, even Phase 1 clinical studies were carried out only with 6 compounds. The first investigations were carried out in 2004 by the Glaxo Group and Amgen with the compounds called GW856464 and AMG-076/071, respectively, with obesity indication. According to the Phase 1b "proof of confidence" investigation of Bristol-Meyers Squibb (2011) the compound BMS-830216 proved to be inactive. The last Phase 1 investigation was launched by Astra-Zeneca in March 2014 and was terminated in October. In most cases the poor pharmatokinetic profile and the CYP induction were responsible for the failor of these compounds.

There is a need for developing such melanin-koncentrating hormon antagonists, which would be suitable for the treatment and/or prevention of obesity, obesity related comorbid conditions and complications, diabetes, metabolic disorders, psychiatric diseases accompanied by weight gain, inflammatory bowel diseases, affective dysfunctions, anxiety disorders, sleep-wake cycle disorders, substance abuse and addictive disorders.

SUMMARY OF THE INVENTION

Our aim was to synthesize new, selective and drug-like MCHR1 antagonists.

Surprisingly it was found, that the synthesized new diazepino-indole derivatives, which were not known in the literature, show MCHR1 antagonist activity profile.

The present invention relates to compounds of the general formula (I), as well as to salts, stereoisomers, geometric isomers, diastereomers, hydrates, solvates, and polymorph modifications thereof

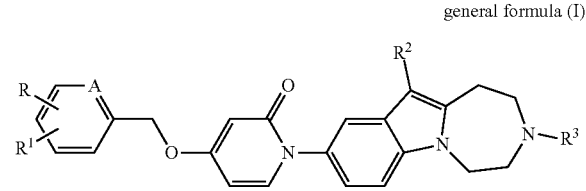

general formula (I)

wherein
the meaning of A is CH or nitrogen atom;
the meaning of R is hydrogen or halogen atom or $C_1$-$C_6$ straight or branched chain alkyl group;
the meaning of $R^1$ is hydrogen or halogen atom or
  $C_1$-$C_6$ straight or branched chain alkyl group, or
  $C_1$-$C_6$ straight or branched chain alkoxy group, or
  mono- or polyhalogenated $C_1$-$C_6$ straight or branched chain haloalkyl group;
the meaning of $R^2$ is hydrogen or halogen atom or
  $C_1$-$C_6$ straight or branched chain alkyl group, or
  $C_1$-$C_6$ straight or branched chain alkoxy group or
  mono- or polyhalogenated $C_1$-$C_4$ straight or branched chain haloalkyl group;
the meaning of $R^3$ is hydrogen or
  $C_1$-$C_6$ straight or branched chain alkyl group, optionally substituted with $C_3$-$C_6$ cycloalkyl group, or
  mono- or polyhalogenated $C_1$-$C_6$ straight or branched chain haloalkyl group; or
  $C_3$-$C_6$ cycloalkyl group, or
  $C_1$-$C_6$ straight or branched chain alkanoyl group.

The invention further relates to pharmaceutical compositions containing a compound of the general formula (I).

According to a further embodiment the compounds of the general formula (I) of the present invention or the pharmaceutical compositions containing them can be used for the treatment and/or prevention of obesity, obesity related comorbid conditions and complications, diabetes, metabolic disorders, psychiatric diseases accompanied by weight gain, inflammatory bowel diseases, affective dysfunctions, anxiety disorders, sleep-wake cycle disorders, substance abuse and addictive disorders.

The present invention further relates to the use of compounds of the general formula (I) for manufacturing pharmaceutical compositions, which can be used for the treatment and/or prevention of obesity, obesity related comorbid conditions and complications, diabetes, metabolic disorders, psychiatric diseases accompanied by weight gain, inflammatory bowel diseases, affective dysfunctions, anxiety disorders, sleep-wake cycle disorders, substance abuse and addictive disorders.

DETAILED DESCRIPTION OF THE INVENTION

The present invention relates to compounds of the general formula (I), as well as to salts, stereoisomers, geometric isomers, diastereomers, hydrates, solvates, and polymorph modifications thereof

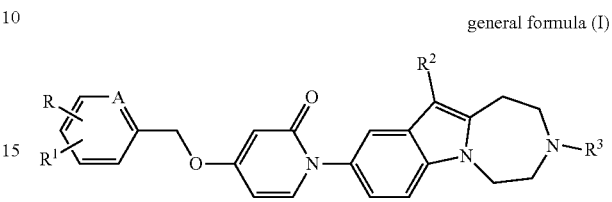

general formula (I)

wherein
the meaning of A is CH or nitrogen atom;
the meaning of R is hydrogen or halogen atom or $C_1$-$C_6$ straight or branched chain alkyl group;
the meaning of $R^1$ is hydrogen or halogen atom or
  $C_1$-$C_6$ straight or branched chain alkyl group, or
  $C_1$-$C_6$ straight or branched chain alkoxy group, or
  mono- or polyhalogenated $C_1$-$C_6$ straight or branched chain haloalkyl group;
the meaning of $R^2$ is hydrogen or halogen atom or
  $C_1$-$C_6$ straight or branched chain alkyl group, or
  $C_1$-$C_6$ straight or branched chain alkoxy group or
  mono- or polyhalogenated $C_1$-$C_4$ straight or branched chain haloalkyl group;
the meaning of $R^3$ is hydrogen or
  $C_1$-$C_6$ straight or branched chain alkyl group, optionally substituted with $C_3$-$C_6$ cycloalkyl group, or
  mono- or polyhalogenated $C_1$-$C_6$ straight or branched chain haloalkyl group; or
  $C_3$-$C_6$ cycloalkyl group, or
  $C_1$-$C_6$ straight or branched chain alkanoyl group.

We note that the term "alkyl group" as used herein refers to $C_1$-$C_6$ straight or branched chain alkyl groups.

The term "alkoxy" as used herein refers to —O-alkyl groups, wherein the meaning of alkyl groups is as defined above.

The term "halogen atom" as used herein refers to for example fluorine, chlorine, bromine or iodine, preferably fluorine, chlorine or bromine, more preferably fluorine or chlorine.

The term "cycloalkyl" or "$C_3$-$C_6$ cycloalkyl" as used herein refers to monovalent carbocyclic groups of 3 to 6 carbons, preferably 3 to 5 carbons, for example, cyclopropyl, cyclobutyl, cyclopentyl and cyclohexyl groups, cyclobutyl and cyclopropyl groups are particularly preferred.

The term "haloalkyl" or "$C_1$-$C_6$ haloalkyl group" as used herein refers to such alkyl groups, which are substituted with one or more halogen atom(s), preferably with fluorine atom(s). Halogen-(short-chained alkyl) groups are for example —$CF_3$, —$CHF_2$, —$CH_2Cl$, —$CH_2CH_2F$, —$CH_2CF_3$, —$CH(CF_3)_2$, —$CF_2$—$CF_3$ groups as well as the groups specifically described in the examples.

The term "alkanoyl" as used herein refers to alkyl-C(O)— groups, wherein the meaning of term "alkyl" is as defined above and the "alkyl" group is single bonded to the carbon atom of the —C(O)— carbonyl group.

A preferred group of compounds comprises those compounds of the general formula (I) wherein the meaning of $R^3$ is:
hydrogen atom or acetyl group,
$C_1$-$C_4$ straight or branched chain alkyl group, optionally substituted with $C_3$-$C_6$ cycloalkyl group,
$C_3$-$C_6$ cycloalkyl group, or
$C_1$-$C_4$ straight or branched chain haloalkyl group.

A further preferred group of compounds comprises those compounds of the general formula (I) wherein the meaning of $R^3$ is:
hydrogen atom,
$C_1$-$C_4$ straight or branched chain alkyl group, optionally substituted with $C_3$-$C_4$ cycloalkyl group or fluorine atom, or
$C_3$-$C_4$ cycloalkyl group.

A more preferred group of compounds comprises those compounds of the general formula (I) wherein the meaning of $R^3$ is methyl, ethyl, isopropyl, cyclopropylmethyl, cyclobutyl or fluoroethyl group, most preferably isopropyl or cyclopropylmethyl groups.

A preferred group of compounds comprises those compounds of the general formula (I) wherein the meaning of $R^2$ is hydrogen or halogen atom or trifluoromethyl or $C_1$-$C_3$ alkyl group, more preferably hydrogen, fluorine or chlorine atom or methyl group, most preferably hydrogen atom.

A further preferred group of compounds comprises those compounds of the general formula (I) wherein the meaning of $R^1$ is:
hydrogen or halogen atom,
$C_1$-$C_4$ straight or branched chain alkyl group, optionally substituted with one or more halogen atom(s) or
$C_1$-$C_3$ alkoxy group.

A further preferred group of compounds comprises those compounds of the general formula (I) wherein the meaning of $R^1$ is hydrogen, fluorine or chlorine atom or methoxy or trifluoromethyl group, more preferably hydrogen, fluorine or chlorine atom.

Another preferred group of compounds comprises those compounds of the general formula (I) wherein the meaning of R is preferably hydrogen atom.

A preferred group of compounds comprises those compounds of the general formula (I) wherein the meaning of R is hydrogen atom and $R^1$ is chlorine atom.

A further preferred group of compounds comprises those compounds of the general formula (I) wherein the above mentioned preferred embodiments of substituents $R^3$, $R^2$, $R^1$, R are optionally combined. In preferred embodiments of the invention the meaning of A substituent can either be CH group or nitrogen atom. The optional combination of the above mentioned more preferred or most preferred embodiments of substituents $R^3$, $R^2$, $R^1$, R also comprises more preferred and most preferred groups of compounds of the general formula (I).

A preferred group of compounds comprises for example the following compounds of the general formula (I) and pharmaceutically acceptable salts thereof:
4-[(5-chloro-pyridin-2-yl)methoxy]-1-{1H,2H,3H,4H,5H-[1,4]diazepino[1,7-a]indol-9-yl}-1,2-dihydropyridin-2-one
4-[(5-chloro-pyridin-2-yl)methoxy]-1-{3-methyl-1H,2H,3H,4H,5H-[1,4]diazepino[1,7-a]indol-9-yl}-1,2-dihydropyridin-2-one
4-[(5-chloro-pyridin-2-yl)methoxy]-1-{3-ethyl-1H,2H,3H,4H,5H-[1,4]diazepino[1,7-a]indol-9-yl}-1,2-dihydropyridin-2-one
4-[(5-fluoro-pyridin-2-yl)methoxy]-1-[3-(propan-2-yl)-1H,2H,3H,4H,5H-[1,4]diazepino[1,7-a]indol-9-yl]-1,2-dihydropyridin-2-one
4-(benzyloxy)-1-[3-(propan-2-yl)-1H,2H,3H,4H,5H-[1,4]diazepino[1,7-a]indol-9-yl]-1,2-dihydropyridin-2-one
4-[(5-chloro-pyridin-2-yl)methoxy]-1-[3-(propan-2-yl)-1H,2H,3H,4H,5H-[1,4]diazepino[1,7-a]indol-9-yl]-1,2-dihydropyridin-2-one
4-[(4-fluoro-phenyl)methoxy]-1-[3-(propan-2-yl)-1H,2H,3H,4H,5H-[1,4]diazepino[1,7-a]indol-9-yl]-1,2-dihydropyridin-2-one
4-[(4-chloro-phenyl)methoxy]-1-[3-(propan-2-yl)-1H,2H,3H,4H,5H-[1,4]diazepino[1,7-a]indol-9-yl]-1,2-dihydropyridin-2-one
4-[(2-fluoro-phenyl)methoxy]-1-[3-(propan-2-yl)-1H,2H,3H,4H,5H-[1,4]diazepino[1,7-a]indol-9-yl]-1,2-dihydropyridin-2-one
1-[11-chloro-3-(propan-2-yl)-1H,2H,3H,4H,5H-[1,4]diazepino[1,7-a]indol-9-yl]-4-[(5-chloro-pyridin-2-yl)methoxy]-1,2-dihydropyridin-2-one
4-(benzyloxy)-1-[11-chloro-3-(propan-2-yl)-1H,2H,3H,4H,5H-[1,4]diazepino[1,7-a]indol-9-yl]-1,2-dihydropyridin-2-one
4-[(5-chloro-pyridin-2-yl)methoxy]-1-[3-(cyclopropylmethyl)-1H,2H,3H,4H,5H-[1,4]diazepino[1,7-a]indol-9-yl]-1,2-dihydropyridin-2-one
4-[(5-chloro-pyridin-2-yl)methoxy]-1-{3-cyclopropyl-1H,2H,3H,4H,5H-[1,4]diazepino[1,7-a]indol-9-yl}-1,2-dihydropyridin-2-one
4-[(5-chloro-pyridin-2-yl)methoxy]-1-{3-cyclobutyl-1H,2H,3H,4H,5H-[1,4]diazepino[1,7-a]indol-9-yl}-1,2-dihydropyridin-2-one
4-[(5-chloro-pyridin-2-yl)methoxy]-1-[11-methyl-3-(propan-2-yl)-1H,2H,3H,4H,5H-[1,4]diazepino[1,7-a]indol-9-yl]-1,2-dihydropyridin-2-one The term "pharmaceutically acceptable salt" as used herein refers to acid- or base addition salts of compounds of the general formula (I) that maintain the biological activity and characteristics of the parent compound, and which can be formed with suitable non-toxic organic or inorganic acids or organic or inorganic bases. Acid addition salts can be formed from inorganic acids such as for example hydrochloric acid, hydrogen bromide, hydrogen iodide, sulfuric acid, sulfamic acid, phosphoric acid, nitric acid and perchloric acid, as well as from organic acids such as for example acetic acid, propionic acid, benzoic acid, glycolic acid, phenylacetic acid, salicylic acid, malonic acid, maleic acid, oleinic acid, pamoic acid, palmitic acid, benzenesulfonic acid, toluensulfonic acid, methanesulfonic acid, oxalic acid, tartaric acid, succinic acid, citric acid, malic acid, lactic acid, glutamic acid, fumaric acid and the like. Base addition salts can be formed for example from ammonium-, potassium-, sodium- and quaternery ammonium hydroxides, such as for example tetramethylammonium hydroxide.

The compounds of formula (I) of the present invention can be synthesized according to reaction sequence depicted in scheme 1.

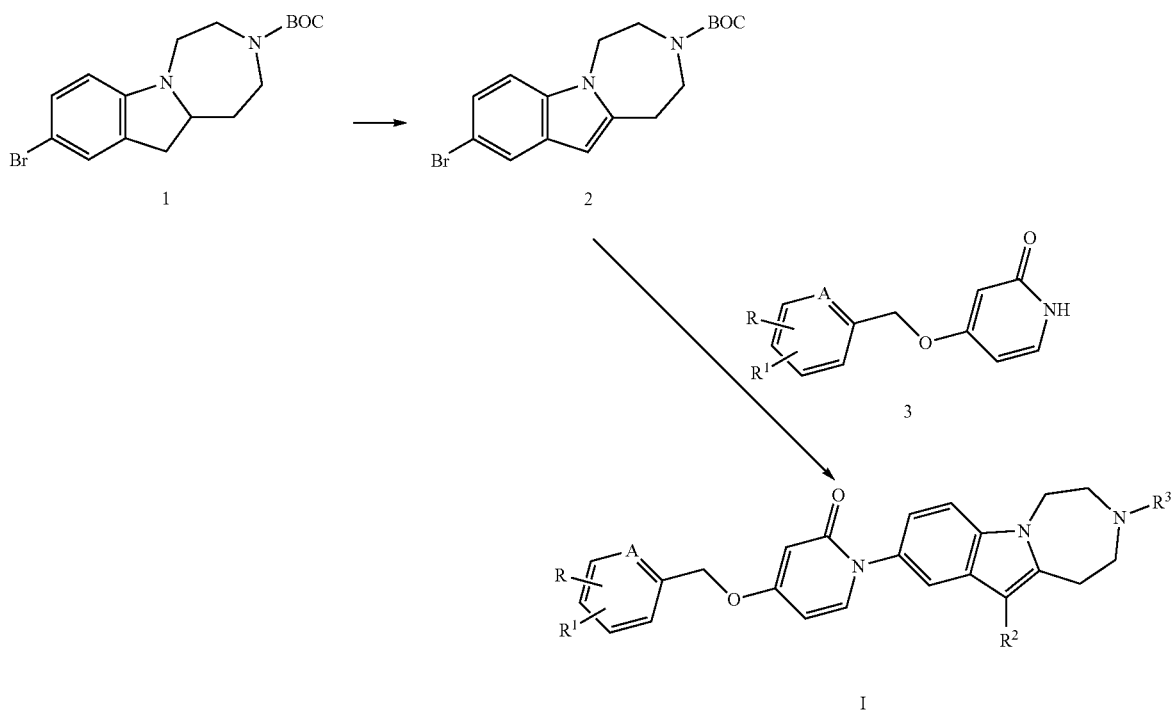

Scheme 1.

Unless otherwise stated the meaning of substituents is as described for the general formula (I).

The intermediate of formula (2) was obtained from compound of formula (1) [Bioorganic & Medicinal Chemistry Letters 13 (2003) 2369-2372; compound of formula (13)] by reacting it with an oxidizing agent, preferably with 5,6-dicyano-2,3-dichloro-1,4-benzoquinone in an inert solvent, preferably in tetrahydrofuran, at room temperature or under cooled reaction conditions, preferably at 0° C.

Compounds of the general formula (I), wherein $R^2$=H, $R^3$=tert-butoxycarbonyl, were synthesized by reacting the compound of formula (2) with a compound of the general formula (3) in the presence of a catalyst, preferably copper (I) iodide, a base, preferably potassium carbonate or cesium carbonate, a ligand, preferably trans-N,N'-dimethylcyclohexane-1,2-diamine, under heated reaction conditions, preferably at 110° C., in an inert solvent, preferably in toluene. When $R^2$=H, and $R^3$=tert-butoxycarbonyl those compounds of the general formula (I) wherein $R^3$=H were obtained after removal of the protective group. When $R^2$=H and $R^3$=H those compounds of the general formula (I) wherein $R^3$=alkyl or haloalkyl were obtained by reductive alkylation, alkylation or haloalkylation. When $R^2$=H, and $R^3$=H those compounds of the general formula (I) wherein $R^3$=acyl were obtained by acylation. When $R^2$=H, and $R^3$=alkyl or haloalkyl those compounds of the general formula (I) wherein $R^2$=halogen were obtained by halogenation. When $R^2$=iodine, and $R^3$=alkyl those compounds of the general formula (I) wherein $R^2$=alkyl were obtained by a palladium catalyzed cross-coupling reaction.

Compounds of the general formula (3), needed for the synthesis of compounds of the general formula (I) of the present invention, were synthesized according to the reaction sequence depicted in scheme 2.

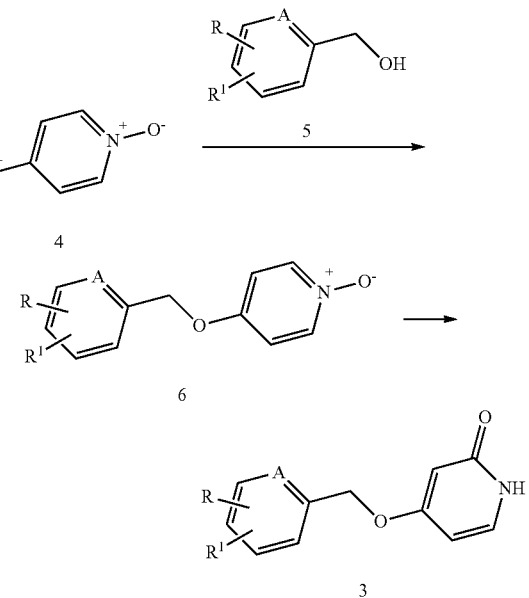

Scheme 2

Compound of formula (4) was reacted with compounds of formula (5) under phase transfer conditions, in the presence of a phase transfer catalyst, preferably benzyltriethylammonium chloride and a base, preferably sodium hydroxide, in a mixture of water and an inert solvent, preferably dichloromethane, at a temperature about from room temperature to reflux temperature, preferably at room temperature, to yield intermediate compounds of the general formula (6). Intermediate compounds of the general formula (3) were synthesized by reacting compounds of the general formula (6) with acetic anhydride at reflux temperature, then with methanol and ethyl acetate at a temperature about from room temperature to reflux temperature, preferably at reflux temperature.

Reagents required for the above reactions and the details of synthetic steps are described in the examples.

One embodiment of the present invention is the new intermediate of formula (2), the tert-butyl 9-bromo-1H,2H,3H,4H,5H-[1,4]diazepino[1,7-a]indol-3-carboxylate, synthesized in the process for the synthesis of compounds of the general formula (I).

The present invention also relates to the pharmaceutical compositions having melanin-concentrating hormone receptor 1 antagonistic activity, containing a compound of the general formula (I) or salts thereof as active ingredient in therapeutically effective amount together with one or more pharmaceutically applicable excipients and/or solvent.

The pharmaceutical compositions can be in single dosage forms containing predetermined amount of active ingredient. This dosage can contain the therapeutically effective amount of compound of the general formula (I) or salt thereof or a given percentage of the therapeutically effective amount in such a way that these single dosage forms for repeated administration can be administered over a given period of time in order to reach the desired therapeutically effective dose. Preferred single dosage forms are those which contain the daily dose or sub-dose or—as it was mentioned above—a given percentage of the active ingredient. Furthermore these pharmaceutical compositions can be manufactured in any pharmacy by known methods.

The term "therapeutically effective amount" as used herein refers to the amount of the active ingredient—compared to the subject, who did not receive such an amount—which results in the improved treatment, curing, prevention or improvement of an illness or pathological condition or side-effect, or suppresses the degree of progression of an illness or pathological condition. The term includes the effective amounts required for improving normal physiological functions as well. In the therapeutic applications compounds of the general formula (I) or salts thereof can be administered in therapeutically effective amount as unformulated drug substances or the active ingredient can be formulated as medicament.

The exact therapeutically effective amount of compounds of the present invention or salts thereof depends on several factors, including—but not exclusively—the age and the bodyweight of the treated subject (patient), the type and the seriousness of the disease to be treated, the type of the pharmaceutical composition/medicament and the way of administration.

Furthermore the present invention relates to the process for the treatment and/or prevention of disorders or conditions associated with melanin-concentrating hormone receptor 1 activity, such treatment comprises the step of administering a therapeutically effective amount of the compound of the general formula (I) or therapeutically acceptable salt thereof as such or in combination with a therapeutically acceptable carrier and/or solvent as pharmaceutical composition to a subject in need, preferably to a mammal, more preferably to a human. The aforementioned processes are preferably used for the treatment and/or prevention of diseases or conditions associated with the melanin concentrating hormone receptor 1 function, such as obesity, obesity related comorbid conditions and complications, diabetes, metabolic disorders, psychiatric diseases accompanied by weight gain, inflammatory bowel diseases, affective dysfunctions, anxiety disorders, sleep-wake cycle disorders, substance abuse and addictive disorders.

The term "treatment" as used herein refers to preventing and alleviating the specified pathological condition, eliminating or reducing one or more symptoms of the condition, slowing or eliminating the progression of the condition, and preventing or delaying the reoccurrence of the condition in a previously afflicted or diagnosed patient or subject. The profilaxis (or prevention, or the delaying of the disease) can be achieved by administering the drug the same way or similarly as in the case of patients who suffer from manifested disease or condition.

The present invention relates to the treatment of subjects, preferably mammals, more preferably humans who suffer from obesity, obesity related comorbid conditions and complications, diabetes, metabolic disorders, psychiatric diseases accompanied by weight gain, inflammatory bowel diseases, affective dysfunctions, anxiety disorders, sleep-wake cycle disorders, substance abuse and addictive disorders or a combination of these diseases.

Such treatment comprises the step of administering a therapeutically effective amount of the compound of the general formula (I) or a salt thereof to a subject in need, preferably to a mammal, more preferably to a human. Such treatment can also comprise the step of administering a therapeutically effective amount of a pharmaceutical composition containing a compound of the general formula (I), or a salt thereof to a subject in need, prefereably to a mammal, more preferably to a human.

The term "effective amount" as used herein refers to an amount of a drug or active ingredient which is sufficient, in the subject to which it is administered, to elicit the biological or medical response of a tissue, system, animal (including human) that is being sought, for instance, by a researcher or clinician.

The compounds of the present invention can be administered by any appropriate route, for example, by the oral, rectal, transdermal, subcutaneous, local, intravenous, intramuscular, or intranasal route.

The pharmaceutical compositions of the present invention can be formulated in many ways, for instance as tablet, capsule, powder, suspension, emulsion, solution, syrup, aerosol (with a solid or a liquid carrier) soft or hard gelatin capsule, suppositorie, injection in a steril form.

Pharmaceutically suitable excipiens can be for example the following: starch, cellulose, talcum, glucose, lactose, gelatin, malt, rice-flour, chalk, silikagel, magnesium stearate, sodium stearate, glycerin monostearate, sodium cloride, dried skimmed milk, glycerin, propyleneglycol, water, ethanol and like. The usual pharmaceutical ingredients, for example conservation agents, stabilizing agents, moisturizing or emulsifying agents, salts for adjusting the osmotic pressure, buffers, and the like can be added to the pharmaceutical composition.

The suitable auxiliaries and carrier agents as well as the production methods of the pharmaceutical compositions are known for a person skilled in the art or can be found in the literature.

EXAMPLES

The following examples are intended for illustration only and are not intended to limit the scope of the invention in any way.

From the above description and examples a person skilled in the art would recognize the basic principles of the present invention and can carry on certain alterations and modifications without varying the essential features and contents of the invention in order to adapt the invention for different applications and conditions. Consequently the present invention is not limited to the following examples, but the scope of the invention is defined by the claims which follow.

Generally compounds of the general formula (I) can be synthesized according to the knowledge of a person skilled in the art and/or according to methods described in the examples and/or by similar processes to either. Solvents, temperatures, pressures and other reaction conditions can easily be determined by a person skilled in the art. Starting materials are commercially available and/or can be prepared according to procedures in the literature. During the synthesis of compounds combinatorical methods can also be used, for example in that case when the functional groups of the obtained intermediates are suitable for the application of this methods.

Mass spectra and $^1$H NMR data of examples are given in all cases.

Reference Example 1 tert-butyl 9-bromo-1H,2H,3H,4H,5H-[1,4]diazepino [1,7-a]indol-3-carboxylate (a) Synthesis of tert-butyl 1H,2H,3H,4H,5H,11H, 11aH-[1,4]diazepino[1,7-a]indol-3-carboxylate To a solution of 3.4 g (18 mmol) of 1H,2H,3H,4H,5H, 11H,11aH-[1,4]diazepino[1,7-a]indol [WO0172752 Example 1, step 6] in 170 ml of dichloromethane 3.8 ml (27.09 mmol) of triethylamine was added, then a solution of 4.73 g (21.67 mmol) of di-tert-butyl-dicarbonate in 25 ml of dichloromethane was added dropwise at 0° C. The reaction mixture was stirred at room temperature for 3.5 h, then 150 ml of saturated NaHCO$_3$ solution was added, the phases were separated and the water phase was extracted with 2×50 ml of dichloromethane. The combined organic phases were washed with 50 ml of brine, dried over anhydrous Na$_2$SO$_4$, filtered and concentrated in vacuum. The crude product was purified by flash column chromatography using Kieselgel 60 (0.040-0.063 mm) as adsorbent (Merck) and a 4:1 mixture of hexane and ethyl acetate as eluent to yield 4.88 g (94%) of tert-butyl 1H,2H,3H,4H,5H,11H,11aH-[1,4]diazepino[1,7-a]indol-3-carboxylate. MS (EI) 289.2 [M+H]$^+$.

(b) Synthesis of tert-butyl 9-bromo-1H,2H,3H,4H, 5H,11H,11aH-[1,4]diazepino[1,7-a]indol-3-carboxylate To a solution of 4.87 g (16.9 mmol) of tert-butyl 1H,2H, 3H,4H,5H,11H,11aH-[1,4]diazepino[1,7-a]indol-3-carboxylate [Reference example 1, step (a)] in 160 ml of acetonitrile a solution of 3 g (16.9 mmol) of N-bromosuccinimide in 45 ml of acetonitrile was added dropwise at 0° C. The reaction mixture was stirred at room temperature for 2.5 h, then 1 ml of acetone was added, stirring was continued for 5 min, then the reaction mixture was concentrated in vacuum. The residue was purified by column chromatography using Kieselgel 60 (0.040-0.063 mm) as adsorbent (Merck) and a 95:5 mixture of cyclohexane and acetone as eluent to yield 4.96 g (80%) of tert-butyl 9-bromo-1H,2H,3H,4H,5H,11H,11aH-[1,4]diazepino[1,7-a]indol-3-carboxylate. MS (EI) 367.1 [M+H]$^+$.

(c) Synthesis of tert-butyl 9-bromo-1H,2H,3H,4H, 5H-[1,4]diazepino[1,7-a]indol-3-carboxylate To a solution of 4.95 g (13.5 mmol) of tert-butyl 9-bromo-1H,2H,3H,4H,5H,11H,11aH-[1,4]diazepino[1,7-a]indol-3-carboxylate [Reference example 1, step (b)] in 120 ml of tetrahydrofuran 3.37 g (14.8 mmol) of 5,6-dicyano-2,3-dichloro-1,4-benzoquinone was added in small portions at 0° C., then the reaction mixture was stirred at 0° C. for 45 min. 320 ml of 2 M aqueous sodium hydroxide was added to the reaction mixture, the phases were separated and the water phase was extracted with 3×120 ml of ethyl acetate. The combined organic phases were washed with 2×60 ml of water, 1×120 ml of brine, then dried over anhydrous Na$_2$SO$_4$, filtered and concentrated in vacuum. The crude product was dissolved in 25 ml of ethanol at reflux temperature, then the solid product separated at room temperature was filtered, washed with ethanol and hexane and dried to yield 4.05 g (82%) of the title compound. MS (EI) 387.0 [M+Na]$^+$.

Reference Example 2

4-[(2-fluorobenzyl)oxy]pyridin-2(1H)-one (a) Synthesis of 4-[(2-fluorobenzyl)oxy]pyridine 1-oxide To a solution of 7.74 g (61.4 mmol) of 2-fluoro-benzyl alcohol and 8.6 g (61.4 mmol) of 4-nitro-pyridin-N-oxide in 140 ml of dichloromethane 0.392 g (1.72 mmol) of benzyltriethylammonium chloride and 81 ml of 9 N aqueous NaOH solution were added at 0° C. The reaction mixture was stirred at room temperature overnight. After addition of dichloromethane and water the phases were separated, the water phase was extracted twice with dichloromethane, the combined organic phases were dried over anhydrous Na$_2$SO$_4$, filtered and concentrated in vacuum. The crude product was dissolved in 350 ml of ethyl acetate at reflux temperature, then the solid product separated at room temperature was filtered, washed with cold ethyl acetate and dried to yield 7.85 g (58%) of 4-[(2-fluorobenzyl)oxy] pyridine 1-oxide. MS (EI) 220.1 [M+H]$^+$.

(b) Synthesis of 4-[(2-fluorobenzyl)oxy]pyridin-2 (1H)-one

A mixture of 7.85 g (35.8 mmol) of 4-[(2-fluorobenzyl) oxy]pyridine 1-oxide [Reference example 2, step (a)] and 125 ml (1.33 mol) of acetic anhydride was refluxed for 4 h, then concentrated in vacuum. 142 ml of ethyl acetate and 28 ml of methanol were added to the residue and the so obtained mixture stirred at reflux temperature for 1 h, then concentrated in vacuum. 63 ml of ethyl acetate was added to the residue and the so obtained suspension was stirred at room temperature overnight. The solid material was filtered, washed with cold ethyl acetate and dried. The crude product was purified by flash column chromatography using Kieselgel 60 (0.040-0.063 mm) as adsorbent (Merck) and a 10:1 mixture of dichloromethane and methanol as eluent to yield 2.95 g (37%) of the title compound. MS (EI) 220.1 [M+H]$^+$.

Reference Example 3

4-[(4-methoxybenzyl)oxy]pyridin-2(1H)-one (a) Synthesis of 4-[(4-methoxybenzyl)oxy]pyridine 1-oxide To a solution of 7.87 g (56.96 mmol) of 4-methoxy-benzyl alcohol and 7.98 g (56.96 mmol) of 4-nitro-pyridin-N-oxide in 130 ml of dichloromethane 0.363 g (1.59 mmol) of benzyltriethylammonium chloride and 75 ml of 9 N aqueous NaOH solution were added at 0° C. The reaction mixture was stirred at room temperature overnight. After addition of dichloromethane and water the phases were separated, the water phase was extracted twice with dichloromethane, the combined organic phases were dried over anhydrous $Na_2SO_4$, filtered and concentrated in vacuum. The crude product was refluxed with 350 ml of ethyl acetate, then the solid product separated at room temperature was filtered, washed with cold ethyl acetate and dried to yield 10.06 g (58%) of the title compound. MS (EI) 232.1 $[M+H]^+$.

(b) Synthesis of 4-[(4-methoxybenzyl)oxy]pyridin-2 (1H)-one

A mixture of 10.06 g (43.5 mmol) of 4-[(4-methoxybenzyl)oxy]pyridine 1-oxide [Reference example 3, step (a)] and 152 ml (1.61 mol) of acetic anhydride was stirred at reflux temperature for 4 h, and the next day for further 5 h, then concentrated in vacuum. 173 ml of ethyl acetate and 35 ml of methanol were added to the residue and the so obtained mixture stirred at reflux temperature for 1 h, then concentrated in vacuum. 77 ml of ethyl acetate was added to the residue and the so obtained suspension was stirred at room temperature overnight. The solid material was filtered, washed with cold ethyl acetate and dried. The crude product was purified by flash column chromatography using Kieselgel 60 (0.040-0.063 mm) as adsorbent (Merck) and a 10:1 mixture of dichloromethane and methanol as eluent to yield 2.089 g (20%) of the title compound. MS (EI) 232.1 $[M+H]^+$.

Reference Example 4 tert-butyl 9-{4-[(5-fluoropyridin-2-yl)methoxy]-2-oxo-1,2-dihydropyridin-1-yl}-1H,2H,3H,4H,5H-[1,4]diazepino[1,7-a]indol-3-carboxylate A mixture of 0.51 g (1.4 mmol) of tert-butyl 9-bromo-1H,2H,3H,4H,5H-[1,4]diazepino[1,7-a]indol-3-carboxylate [Reference example 1, step (c)], 0.31 g (1.4 mmol) of 4-[(5-fluoropyridin-2-yl)methoxy]pyridin-2(1H)-one [EP1916239], 0.27 g (1.4 mmol) of copper(I) iodide, 0.64 g (1.96 mmol) of $Cs_2CO_3$, 0.22 ml (1.4 mmol) of trans-N,N'-dimethylcyclohexan-1,2-diamine and 30 ml of toluene was stirred at room temperature for 1 h while nitrogen gas was bubbled through the mixture. Then the reaction flask was sealed with a septum, immersed into an oil bath of 110° C. and the mixture was stirred overnight at this temperature. The reaction mixture was concentrated in vacuum, 14 ml of saturated aqueous ammonium chloride solution was added to the residue and the suspension was stirred at room temperature for 2 h. The solid product was filtered, washed with saturated aqueous ammonium chloride solution and water, then dried. The crude product was purified by flash column chromatography using Kieselgel 60 (0.040-0.063 mm) as adsorbent (Merck) and first dichloromethane, then a 98:2 mixture of dichloromethane and methanol as eluent to yield 0.48 g (68%) of the title compound. MS (EI) 505.2 $[M+H]^+$.

Reference Example 5 tert-butyl 9-{4-[(4-methoxyphenyl)methoxy]-2-oxo-1,2-dihydropyridin-1-yl}-1H,2H,3H,4H,5H-[1,4]diazepino[1,7-a]indol-3-carboxylate The title compound was obtained from tert-butyl 9-bromo-1H,2H,3H,4H,5H-[1,4]diazepino[1,7-a]indol-3-carboxylate [Reference example 1, step (c)] and 4-[(4-methoxy-benzyl)oxy]pyridin-2(1H)-one [Reference example 3, step (b)] according to the method described in Reference example 4. MS (EI) 516.3 $[M+H]^+$.

Reference Example 6 tert-butyl 9-[4-(benzyloxy)-2-oxo-1,2-dihydropyridin-1-il]-1H,2H,3H,4H,5H-[1,4]diazepino[1,7-a]indol-3-carboxylate The title compound was obtained from tert-butyl 9-bromo-1H,2H,3H,4H,5H-[1,4]diazepino[1,7-a]indol-3-carboxylate [Reference example 1, step (c)] and 4-(benzyloxy)pyridin-2(1H)-one according to the method described in Reference example 4. MS (EI) 486.24 $[M+H]^+$.

Reference Example 7 tert-butyl 9-{4-[(5-chloropyridin-2-yl)methoxy]-2-oxo-1,2-dihydropyridin-1-yl}-1H,2H,3H,4H,5H-[1,4]diazepino[1,7-a]indol-3-carboxylate A mixture of 0.92 g (2.52 mmol) of tert-butyl 9-bromo-1H,2H,3H,4H,5H-[1,4]diazepino[1,7-a]indol-3-carboxylate [Reference example 1, step (c)], 0.64 g (2.7 mmol) of 4-[(5-chloropyridin-2-yl)methoxy]pyridin-2(1H)-one [EP1916239], 0.51 g (2.7 mmol) of copper(I) iodide, 1.14 g (3.5 mmol) of $Cs_2CO_3$, 0.43 ml (2.7 mmol) of trans-N,N'-dimethylcyclohexan-1,2-diamine and 50 ml of toluene was stirred at room temperature for 1 h while nitrogen gas was bubbled through the mixture. Then the reaction flask was sealed with a septum, immersed into an oil bath of 110° C. and the mixture was stirred overnight at this temperature. The reaction mixture was poured into a mixture of 165 ml of dichloromethane:methanol:ccNH$_4$OH (9:1:0.1), and the phases were separated. The organic phase was washed with brine portions (each 30 ml) until the separated water phase remained colorless, then dried over anhydrous $Na_2SO_4$, filtered and concentrated in vacuum. The crude product was purified by flash column chromatography using Kieselgel 60 (0.040-0.063 mm) as adsorbent (Merck) and first dichloromethane, then a 98:2 mixture of dichloromethane and methanol as eluent to yield 0.86 g (66%) of the title compound. MS (EI) 521.2 $[M+H]^+$.

Reference Example 8 tert-butyl 9-{4-[(4-fluoro-phenyl)methoxy]-2-oxo-1,2-dihydropyridin-1-yl}-1H,2H,3H,4H,5H-[1,4]diazepino[1,7-a]indol-3-carboxylate The title compound was obtained from tert-butyl 9-bromo-1H,2H,3H,4H,5H-[1,4]diazepino[1,7-a]indol-3-carboxylate [Reference example 1, step (c)] and 4-[(4-fluoro-benzyl)oxy]pyridin-2(1H)-one [EP1916239] according to the method described in Reference example 4. MS (EI) 504.3 $[M+H]^+$.

Reference Example 9 tert-butyl 9-{4-[(4-chloro-phenyl)methoxy]-2-oxo-1,2-dihydropyridin-1-yl}-1H,2H,3H,4H,5H-[1,4]diazepino[1,7-a]indol-3-carboxylate The title compound was obtained from tert-butyl 9-bromo-1H,2H,3H,4H,5H-[1,4]diazepino[1,7-a]indol-3- carboxylate [Reference example 1, step (c)] and 4-[(4-chloro-benzyl)oxy]pyridin-2(1H)-one [EP1916239] according to the method described in Reference example 4. MS (EI) 520.2 [M+H]+.

Reference Example 10 tert-butyl 9-{4-[(2-fluoro-phenyl)methoxy]-2-oxo-1,2-dihydropyridin-1-yl}-1H,2H,3H,4H,5H-[1,4]diazepino[1,7-a]indol-3-carboxylate The title compound was obtained from tert-butyl 9-bromo-1H,2H,3H,4H,5H-[1,4]diazepino[1,7-a]indol-3-carboxylate [Reference example 1, step (c)] and 4-[(2-fluoro-benzyl)oxy]pyridin-2(1H)-one [Reference example 2, step (b)] according to the method described in Reference example 4. MS (EI) 504.2 [M+H]+.

Reference Example 11 tert-butyl 9-(2-oxo-4-{[4-(trifluoromethyl)phenyl]methoxy}-1,2-dihydropyridin-1-yl)-1H,2H,3H,4H,5H-[1,4]diazepino[1,7-a]indol-3-carboxylate A mixture of 0.34 g (0.93 mmol) of tert-butyl 9-bromo-1H,2H,3H,4H,5H-[1,4]diazepino[1,7-a]indol-3-carboxylate [Reference example 1, step (c)], 0.25 g (0.93 mmol) of 4-{[4-(trifluoromethyl)benzyl]oxy}pyridin-2(1H)-one [WO200989482], 0.18 g (0.95 mmol) of copper(I) iodide, 0.42 g (1.3 mmol) of $Cs_2CO_3$, 0.15 ml (0.95 mmol) of trans-N,N'-dimethylcyclohexane-1,2-diamine and 18 ml of toluene was stirred at room temperature for 1 h while nitrogen gas was bubbled through the mixture. Then the reaction flask was sealed with a septum, immersed into an oil bath of 110° C. and the mixture was stirred overnight at this temperature. The reaction mixture was concentrated in vacuum, 14 ml of saturated ammonium chloride solution was added to residue, and the suspension was stirred at room temperature for 1 h. The solid product was filtered, washed with saturated ammonium chloride solution and water, then dried. The crude product was purified by flash column chromatography using Kieselgel 60 (0.040-0.063 mm) as adsorbent (Merck) and first dichloromethane, then a 98:2:0.1 mixture of dichloromethane, methanol and ccNH4OH as eluent. The obtained product was further purified by column chromatography using a 98:2 mixture of dichloromethane and methanol as eluent to yield 0.27 g (52%) of the title compound. MS (EI) 554.3 [M+H]+.

Example 1

1-{1H,2H,3H,4H,5H-[1,4]diazepino[1,7-a]indol-9-yl}-4-[(5-fluoropyridin-2-yl)methoxy]-1,2-dihydropyridin-2-one hydrochloride salt (a) Synthesis of the Free Base
A mixture of 0.48 g (0.95 mmol) of tert-butyl 9-{4-[(5-fluoropyridin-2-yl)methoxy]-2-oxo-1,2-dihydropyridin-1-yl}-1H,2H,3H,4H,5H-[1,4]diazepino[1,7-a]indol-3-carboxylate [Reference example 4], 17 ml of ethyl acetate and 8.2 ml of 20% hydrogen chloride in ethyl acetate was stirred at room temperature overnight. The solid product was filtered, washed with ethyl acetate and diethyl ether, and dried. The crude product was purified by flash column chromatography using Kieselgel 60 (0.040-0.063 mm) as adsorbent (Merck) and first dichloromethane, then a 95:5:1 mixture of dichloromethane, methanol and ccNH4OH as eluent to yield 0.29 g (71%) of 1-{1H,2H,3H,4H,5H-[1,4]diazepino[1,7-a]indol-9-yl}-4-[(5-fluoropyridin-2-yl)methoxy]-1,2-dihydropyridin-2-one as free base. MS (EI) 405.2 [M+H]+.

(b) Synthesis of the Hydrochloride Salt
0.12 g (0.28 mmol) of 1-{1H,2H,3H,4H,5H-[1,4]diazepino[1,7-a]indol-9-yl}-4-[(5-fluoropyridin-2-yl)methoxy]-1,2-dihydropiridin-2-one [Example 1, step (a)] was dissolved in a mixture of 5 ml of methanol and 2 ml of 20%° hydrogen chloride in ethyl acetate, then the reaction mixture was concentrated. The solid residue was triturated with diethyl ether, filtered, washed with diethyl ether and dried to yield 0.089 g (65%) of the title compound. MS (EI) 405.2 [M+H]+. 1H NMR (400 MHz, DMSO-$d_6$) δ: 9.70-9.85 (br m, 2H), 8.63 (d, J=2.9 Hz, 1H), 7.83 (td, J=8.7, 2.9 Hz, 1H), 7.66 (dd, J=8.7, 4.4 Hz, 1H), 7.58 (d, J=7.6 Hz, 1H), 7.54 (d, J=9.0 Hz, 1H), 7.42 (d, J=2.2 Hz, 1H), 7.05 (dd, J=8.6, 2.2 Hz, 1H), 6.42 (s, 1H), 6.13 (dd, J=7.6, 2.8 Hz, 1H), 5.98 (d, J=2.8 Hz, 1H), 5.22 (s, 2H), 4.62-4.70 (br m, 2H), 3.31-3.39 (br m, 4H), 3.22-3.31 (br m, 2H).

Example 2

1-{1H,2H,3H,4H,5H-[1,4]diazepino[1,7-a]indol-9-yl}-4-[(4-methoxyphenyl)-methoxy]-1,2-dihydropyridin-2-one hydrochloride salt (a) Synthesis of the Hydrochloride Salt
A mixture of 0.44 g (0.85 mmol) of ter-butyl 9-{4-[(4-methoxyphenyl)-methoxy]-2-oxo-1,2-dihydropyridin-1-yl}-1H,2H,3H,4H,5H-[1,4]diazepino[1,7-a]-indol-3-carboxylate [Reference example 5], 13 ml of ethyl acetate, 1.95 ml of 20% hydrogen chloride in ethyl acetate and 20 ml of methanol was stirred at room temperature for 3 h, then 20 ml of methanol was added and stirring was continued for 3 days. The solid product was filtered, washed with diethyl ether and dried to yield 0.078 g (20%) of the title compound. MS (EI) 416.2 [M+H]+. 1H NMR (400 MHz, DMSO-$d_6$) δ: 9.39-9.53 (br m, 2H), 7.50-7.56 (m, 2H), 7.38-7.43 (m, 3H), 7.04 (dd, J=8.7, 2.1 Hz, 1H), 6.95-7.00 (m, 2H), 6.42 (s, 1H), 6.04 (dd, J=7.6, 2.7 Hz, 1H), 5.95 (d, J=2.7 Hz, 1H), 5.05 (s, 2H), 4.58-4.66 (m, 2H), 3.77 (s, 3H), 3.33-3.41 (br m, 2H), 3.24-3.33 (br m, 4H). Concentration of the filtrate resulted in further 0.26 g (67%) of the title compound.

(b) Synthesis of the Free Base
A mixture of 0.32 g (0.71 mmol) of 1-{1H,2H,3H,4H,5H-[1,4]diazepino[1,7-a]indol-9-yl}-4-[(4-methoxyphenyl)methoxy]-1,2-dihydropyridin-2-one hydrochoride [Example 2, step (a)], 40 ml of a 9:1 mixture of dichloromethane and 2-propanol and 5% aqueous $NaHCO_3$ solution (pH=8-9) was stirred at room temperature for 10 min, then the phases were separated. The water phase was extracted with 30 ml of a 9:1 mixture of dichloromethane and 2-propanol. The combined organic phases were washed with 30 ml of brine, then dried over anhydrous $Na_2SO_4$, filtered and concentrated in vacuum. The crude product was crystallized with ethanol, the solid product was filtered and washed with ethanol to yield 0.097 g (33%) of 1-{1H,2H,3H,4H,5H-[1,4]diazepino[1,7-a]indol-9-yl}-4-[(4-methoxyphenyl)methoxy]-1,2-dihydropyridin-2-one as free base. MS (EI) 416.2 [M+H]+.

Concentration of the mother liquid resulted in further 0.08 g (27%) of the free base.

Example 3

4-(benzyloxy)-1-{1H,2H,3H,4H,5H-[1,4]diazepino[1,7-a]indol-9-yl}-1,2-dihydropyridin-2-one maleic acid salt (a) Synthesis of the Hydrochloride Salt A mixture of 0.65 g (1.34 mmol) of tert-butyl 9-[4-(benzyloxy)-2-oxo-1,2-dihydropyridin-1-yl]-1H,2H,3H,4H,5H-[1,4]diazepino[1,7-a]indol-3-carboxylate [Reference example 6], 20 ml of ethyl acetate and 6 ml of 20% hydrogen chloride in ethyl acetate was stirred at room temperature for 2 h, then 6 ml of 200 hydrogen chloride in ethyl acetate was added and the mixture was stirred at room temperature overnight. The solid product was filtered, washed with ethyl acetate and diethyl ether and dried to yield 0.62 g (100%) of 4-(benzyloxy)-1-{1H,2H,3H,4H,5H-[1,4]diazepino[1,7-a]indol-9-yl}-1,2-dihydropyridin-2-one hydrochloride salt. MS (EI) 386.2 [M+H]+.

(b) Synthesis of the Free Base

A mixture of 0.58 g (1.37 mmol) of 4-(benzyloxy)-1-{1H,2H,3H,4H,5H-[1,4]diazepino[1,7-a]indol-9-yl}-1,2-dihydropyridin-2-one hydrochloride [Example 3, step (a)], 14 ml of 5% aqueous $NaHCO_3$ solution and 40 ml of a 9:1 mixture of dichloromethane and 2-propanol was stirred at room temperature for 10 min, then the phases were separated. The water phase was extracted with 2×12 ml of a 9:1 mixture of dichloromethane and 2-propanol. The combined organic phases were washed with 15 ml of brine, then dried over anhydrous $Na_2SO_4$, filtered and concentrated in vacuum to yield 0.44 g (83%) of 4-(benzyloxy)-1-{1H,2H,3H,4H,5H-[1,4]diazepino[1,7-a]indol-9-yl}-1,2-dihydropyridin-2-one as free base. MS (EI) 386.2 [M+H]+.

(c) Synthesis of the Maleic Acid Salt

To a solution of 0.21 g (0.54 mmol) of 4-(benzyloxy)-1-{1H,2H,3H,4H,5H-[1,4]diazepino[1,7-a]indol-9-yl}-1,2-dihydropyridin-2-one [Example 3, step (b)] in a 10:1 mixture of dichloromethane and methanol 0.078 g (0.67 mmol) of maleic acid was added and the reaction mixture was concentrated. The solid residue was triturated with ethanol, filtered, washed with ethanol and diethyl ether and dried to yield 0.218 g (80%) of the title compound. MS (EI) 386.2 [M+H]+. $^1$H NMR (400 MHz, DMSO-$d_6$) δ: 8.80-9.15 (br m, 1.6H), 7.51-7.56 (m, 2H), 7.34-7.49 (m, 6H), 7.05 (dd, J=8.7, 2.1 Hz, 1H), 6.43 (s, 1H), 6.08 (dd, J=7.6, 2.7 Hz, 1H), 6.04 (s, 2.2H), 5.95 (d, J=2.7 Hz, 1H), 5.14 (s, 2H), 4.50-4.62 (br m, 2H), 3.20-3.45 (m, 6H).

Example 4

4-[(5-chloropyridin-2-yl)methoxy]-1-{1H,2H,3H,4H,5H-[1,4]diazepino[1,7-a]indol-9-yl}-1,2-dihydropyridin-2-one dihydrochloride salt (a) Synthesis of the Dihydrochloride Salt A mixture of 1.32 g (2.54 mmol) of tert-butyl 9-{4-[(5-chloropyridin-2-yl)methoxy]-2-oxo-1,2-dihydropyridin-1-yl}-1H,2H,3H,4H,5H-[1,4]diazepino[1,7-a]indol-3-carboxylate [Reference example 7], 15 ml of methanol, 1.25 M hydrogen chloride in methanol and 30 ml of 20% hydrogen chloride in ethyl acetate was stirred at room temperature overnight. The solid product was filtered, washed with diethyl ether and dried to yield 1.26 g (100%) of the title compound. MS (EI) 421.1 [M+H]+. $^1$H NMR (400 MHz, DMSO-$d_6$) δ: 9.72-9.82 (br m, 2H), 8.68 (d, J=2.5 Hz, 1H), 8.03 (dd, J=8.2, 2.5 Hz, 1H), 7.51-7.64 (m, 3H), 7.42 (d, J=2.0 Hz, 1H), 7.05 (dd, J=8.8, 2.2 Hz, 1H), 6.42 (s, 1H), 6.00-6.40 (br m, the signal of HCl overlapped by the signal of $H_2O$; 1H), 6.13 (dd, J=7.5, 2.6 Hz, 1H), 5.96 (d, J=2.7 Hz, 1H), 5.23 (s, 2H), 4.62-4.70 (m, 2H), 3.22-3.40 (m, 6H).

(b) Synthesis of the Free Base

A mixture of 4.44 g (8.52 mmol) of tert-butyl 9-{4-[(5-chloropyridin-2-yl)methoxy]-2-oxo-1,2-dihydropyridin-1-yl}-1H,2H,3H,4H,5H-[1,4]diazepino[1,7-a]indol-3-carboxylate [Reference example 7], 130 ml of ethyl acetate and 20 ml of 20%° hydrogen chloride in ethyl acetate was stirred at room temperature for 2 h. The solid product was filtered, washed with ethanol and diethyl ether and dried. 85 ml of 5% aqueous $NaHCO_3$ solution and 250 ml of a 9:1 mixture of dichloromethane and 2-propanol were added to the crude product, the phases were separated, the water phase was extracted with 2×80 ml of a 9:1 mixture of dichloromethane and 2-propanol. The combined organic phases were washed with 80 ml of brine, then dried over anhydrous $Na_2SO_4$, filtered and concentrated in vacuum. 50 ml of diethyl ether was added to the residue and the mixture was stirred at room temperature overnight. The solid product was filtered, washed with diethyl ether and dried to yield 3.39 g (95%) of 4-[(5-chloropyridin-2-yl)methoxy]-1-{1H,2H,3H,4H,5H-[1,4]diazepino[1,7-a]indol-9-yl}-1,2-dihydropyridin-2-one as free base. MS (EI) 421.2 [M+H]+.

Example 5

1-{1H,2H,3H,4H,5H-[1,4]diazepino[1,7-a]indol-9-yl}-4-[(4-fluorophenyl)methoxy]-1,2-dihydropyridin-2-one hydrochloride salt (a) Synthesis of the Free Base A mixture of 0.28 g (0.55 mmol) of tert-butyl 9-{4-[(4-fluorophenyl)methoxy]-2-oxo-1,2-dihydropyridin-1-yl}-1H,2H,3H,4H,5H-[1,4]diazepino[1,7-a]indol-3-carboxylate [Reference example 8], 10 ml of ethyl acetate and 1.25 ml of 20% hydrogen chloride in ethyl acetate was stirred at room temperature overnight, then 1.25 ml of 20% hydrogen chloride in ethyl acetate was added and the mixture was stirred at room temperature for 2 h. After this 50 ml of methanol was added to the reaction mixture and stirring was continued at room temperature overnight, then the mixture was concentrated. 40 ml of a 9:1 mixture of dichloromethane and 2-propanol and 5% aqueous $NaHCO_3$ solution were added to the residue (pH of the water phase is 8-9), the mixture was stirred at room temperature for 10 min, then the phases were separated. The water phase was extracted with 30 ml of a 9:1 mixture of dichloromethane and 2-propanol. The combined organic phases were washed with 30 ml of brine, then dried over anhydrous $Na_2SO_4$, filtered and concentrated in vacuum. The crude product was triturated with ethanol, the solid product was filtered and washed with ethanol to yield 0.104 g (46%) of 1-{1H,2H,3H,4H,5H-[1,4]diazepino[1,7-a]indol-9-yl}-4-[(4-fluorophenyl)methoxy]-1,2-dihydropyridin-2-one as free base. MS (EI) 404.2 [M+H]+.

(b) Synthesis of the Hydrochloride Salt 0.035 g (0.08 mmol) of 1-{1H,2H,3H,4H,5H-[1,4]diazepino[1,7-a]indol-9-yl}-4-[(4-fluorophenyl)methoxy]-1,2-dihydropyridin-2-one [Example 5, step (a)] was dissolved in a mixture of 2 ml of ethanol and 25.5% hydrogen chloride in ethanol (pH=2), then the reaction mixture was concentrated. The solid residue was triturated with diethyl ether, filtered, washed with diethyl ether and dried to yield 0.021 g (60%) of the title compound. MS (EI) 404.2 [M+H]+. $^1$H NMR (400 MHz, DMSO-$d_6$) δ: 9.22-9.33 (br m, 2H), 7.49-7.56 (m, 4H), 7.42 (d, J=2.1 Hz, 1H), 7.22-7.30 (m, 2H), 7.05 (dd, J=8.6, 2.1 Hz, 1H), 6.42 (s, 1H), 6.06 (dd, J=7.6, 2.7 Hz, 1H), 5.96 (d, J=2.7 Hz, 1H), 5.12 (s, 2H), 4.57-4.63 (m, 2H), 3.34-3.42 (br m, 2H), 3.26-3.33 (m, 4H).

Example 6

4-[(4-chlorophenyl)methoxy]-1-{1H,2H,3H,4H,5H-[1,4]diazepino[1,7-a]indol-9-yl}-1,2-dihydropyridin-2-one hydrochloride salt (a) Synthesis of the Hydrochloride Salt A mixture of 0.6 g (1.15 mmol) of tert-butyl 9-{4-[(4-chlorophenyl)methoxy]-2-oxo-1,2-di hydropyridin-1-yl}-1H,2H,3H,4H,5H-[1,4]diazepino[1,7-a]indol-3-carboxylate [Reference example 9], 20 ml of ethyl acetate and 5 ml of 20% hydrogen chloride in ethyl acetate was stirred at room temperature for 2 h, then 5 ml of 20% hydrogen chloride in ethyl acetate was added and the mixture was stirred at room temperature for 95 min. 5 ml of dichloromethane was added to the reaction mixture and stirring was continued at room temperature overnight. The solid product was filtered, washed with ethyl acetate and diethyl ether, then dried to yield 0.6 g (100%) of the title compound. MS (EI) 420.1 [M+H]$^+$. $^1$H NMR (400 MHz, DMSO-d$_6$) δ: 9.43-9.62 (br m, 2H), 7.51-7.57 (m, 2H), 7.50 (s, 4H), 7.42 (d, J=2.0 Hz, 1H), 7.04 (dd, J=8.7, 2.1 Hz, 1H), 6.42 (s, 1H), 6.08 (dd, J=7.6, 2.7 Hz, 1H), 5.95 (d, J=2.7 Hz, 1H), 5.15 (s, 2H), 4.59-4.67 (m, 2H), 3.24-3.41 (m, 6H).

(b) Synthesis of the Base 0.56 g (1.2 mmol) of 4-[(4-chlorophenyl)methoxy]-1-{1H,2H,3H,4H,5H-[1,4]diazepino[1,7-a]indol-9-yl}-1,2-dihydropyridin-2-one hydrochloride [Example 6, step (a)] was dissolved in a mixture of 15 ml of 5% aqueous NaHCO$_3$ solution and 40 ml of a 9:1 mixture of dichloromethane and 2-propanol. The phases were separated, the water phase was extracted with 1×40 ml, 2×20 ml and 3×40 ml of a 9:1 mixture of dichloromethane and 2-propanol. The combined organic phases were washed with 50 ml of brine, then dried over anhydrous Na$_2$SO$_4$, filtered and concentrated in vacuum to yield 0.44 g (87%) of 4-[(4-chlorophenyl) methoxy]-1-{1H,2H,3H,4H,5H-[1,4]diazepino[1,7-a]indol-9-yl}-1,2-dihydropyridin-2-one as free base. MS (EI) 420.1 [M+H]$^+$.

Example 7

1-{1H,2H,3H,4H,5H-[1,4]diazepino[1,7-a]indol-9-yl}-4-[(2-fluorphenyl)methoxy]-1,2-dihydropyridin-2-one hydrochloride salt (a) Synthesis of the Hydrochloride Salt A mixture of 0.44 g (0.87 mmol) of tert-butyl 9-{4-[(2-fluorophenyl)methoxy]-2-oxo-1,2-dihydropyridin-1-yl}-1H,2H,3H,4H,5H-[1,4]diazepino[1,7-a]indol-3-carboxylate [Reference example 10], 15 ml of ethyl acetate and 8 ml of 20% hydrogen chloride in ethyl acetate was stirred at room temperature overnight. The solid product was filtered, washed with ethyl acetate and diethyl ether, then dried to yield 0.37 g (96%) of the title compound. MS (EI) 404.1 [M+H]$^+$. $^1$H NMR (400 MHz, DMSO-d$_6$) δ: 9.50-9.65 (br m, 2H), 7.40-7.63 (m, 5H), 7.24-7.34 (m, 2H), 7.05 (dd, J=8.8, 2.2 Hz, 1H), 6.42 (s, 1H), 6.06 (dd, J=7.6, 2.8 Hz, 1H), 6.02 (d, J=2.8 Hz, 1H), 5.17 (s, 2H), 4.60-4.68 (m, 2H), 3.23-3.42 (m, 6H).

(b) Synthesis of the Free Base 0.33 g (0.75 mmol) of 1-{1H,2H,3H,4H,5H-[1,4]diazepino[1,7-a]indol-9-yl}-4-[(2-fluorophenyl)methoxy]-1,2-dihydropyridin-2-one hydrochloride [Example 7, step (a)] was dissolved in 15 ml of 5% aqueous NaHCO$_3$ solution and 20 ml of a 9:1 mixture of dichloromethane and 2-propanol. The phases were separated, the water phase was extracted with 2×20 ml of a 9:1 mixture of dichloromethane and 2-propanol. The combined organic phases were washed with 25 ml of brine, then dried over anhydrous Na$_2$SO$_4$, filtered and concentrated in vacuum to yield 0.237 g (78%) of 1-{1H,2H,3H,4H,5H-[1,4]diazepino[1,7-a]indol-9-yl}-4-[(2-fluorophenyl)methoxy]-1,2-dihydropyridin-2-one as free base. MS (EI) 404.2 [M+H]$^+$.

Example 8

1-{1H,2H,3H,4H,5H-[1,4]diazepino[1,7-a]indol-9-il}-4-{[4-(trifluoromethyl)phenyl]methoxy}-1,2-dihydropyridin-2-one hydrochloride salt (a) Synthesis of the Hydrochloride Salt A mixture of 0.27 g (0.46 mmol) of tert-butyl 9-(2-oxo-4-{[4-(trifluoromethyl)phenyl]methoxy}-1,2-dihydropyridin-1-yl)-1H,2H,3H,4H,5H-[1,4]diazepino[1,7-a]indol-3-carboxylate [Reference example 11], 15 ml of ethyl acetate, 1.1 ml of 20% hydrogen chloride in ethyl acetate and 30 ml of methanol was stirred at room temperature for 4 h, then 25 ml of methanol was added and the mixture was stirred at room temperature overnight. Further 1.1 ml of 20% hydrogen chloride in ethyl acetate was added to the reaction mixture and stirring was continued at room temperature for 4 h, then the mixture was concentrated. The residue was triturated with ethyl acetate, the solid product was filtered, washed with ethyl acetate and dried to yield 0.138 g (61%) of the title compound. MS (EI) 454.1 [M+H]$^+$. $^1$H NMR (400 MHz, DMSO-d$_6$) δ: 9.30-9.41 (br m, 2H), 7.78-7.84 (m, 2H), 7.66-7.73 (m, 2H), 7.51-7.58 (m, 2H), 7.42 (d, J=2.2 Hz, 1H), 7.05 (dd, J=8.7, 2.1 Hz, 1H), 6.42 (s, 1H), 6.11 (dd, J=7.6, 2.7 Hz, 1H), 5.95 (d, J=2.7 Hz, 1H), 5.28 (s, 2H), 4.57-4.66 (br m, 2H), 3.33-3.41 (br m, 2H), 3.26-3.33 (m, 4H).

(b) Synthesis of the Free Base 0.21 g (0.43 mmol) of 1-{(1H,2H,3H,4H,5H-[1,4]diazepino[1,7-a]indol-9-yl}-4-{[4-(trifluoromethyl)phenyl]methoxy}-1,2-dihydropyridin-2-one hydrochloride [Example 8, step (a)] was dissolved in a mixture of 6 ml of 5% aqueous NaHCO$_3$ solution and 15 ml of a 9:1 mixture of dichloromethane and 2-propanol. The phases were separated, the water phase was extracted with 2×15 ml of a 9:1 mixture of dichloromethane and 2-propanol. The combined organic phases were washed with 20 ml of brine, then dried over anhydrous Na$_2$SO$_4$, filtered and concentrated in vacuum to yield 0.148 g (76%) of 1-{1H,2H,3H,4H,5H-[1,4]diazepino[1,7-a]indol-9-yl}-4-{[4-(trifluoromethyl)phenyl]methoxy}-1,2-dihydropyridin-2-one as free base. MS (EI) 454.1 [M+H]$^+$.

Example 9

4-[(5-fluoropyridin-2-yl)methoxy]-1-{3-methyl-1H,2H,3H,4H,5H-[1,4]diazepino[1,7-a]indol-9-yl}-1,2-dihydropyridin-2-one maleic acid salt (a) Synthesis of the Free Base A mixture of 0.05 g (0.124 mmol) of 1-{1H,2H,3H,4H,5H-[1,4]diazepino[1,7-a]indol-9-yl}-4-[(5-fluoropyridin-2-yl)methoxy]-1,2-dihydropyridin-2-one [Example 1, step (a)], 2.5 ml of methanol, 0.093 ml (1.24 mmol) of 37% aqueous formaldehide solution and 0.105 g (1.67 mmol) of sodium cyanoborohydride was shaken in a closed reaction vessel at 70° C. for 1 h. 7 ml of saturated aqueous NaHCO$_3$ solution and 15 ml of dichloromethane were added to the reaction mixture, the phases were separated, and the water phase was extracted with 15 ml of dichloromethane. The combined organic phases were dried over anhydrous Na$_2$SO$_4$, filtered and concentrated in vacuum. The crude product was purified by flash column chromatography using Kieselgel 60 (0.040-0.063 mm) as adsorbent (Merck) and first a 98:2:1, then a 95:5:1 mixture of dichloromethane, methanol and ccNH$_4$OH as eluent to yield 0.039 g (76%) of 4-[(5-fluoropyridin-2-yl)methoxy]-1-{3-methyl-1H,2H,3H,4H,5H-[1,4]diazepino[1,7-a]indol-9-yl}-1,2-dihydropyridin-2-one as free base. MS (EI) 419.2 [M+H]$^+$.

(b) Synthesis of the Maleic Acid Salt 0.039 g (0.093 mmol) of 4-[(5-fluoropyridin-2-yl)methoxy]-1-{3-methyl-1H,2H,3H,4H,5H-[1,4]diazepino[1,7-a]indol-9-yl}-1,2-dihydropyridin-2-one free base [Example 9, step (a)] was dissolved in 10 ml of a 9:1 mixture of dichloromethane and ethanol, 0.011 g (0.095 mmol) of maleic acid was added, then the dichloromethane was evaporated in vacuum. Diethyl ether was added to the residue, the solid product was filtered, washed with diethyl ether and dried to yield 0.030 g (60%) of the title compound. MS (EI) 419.2 [M+H]$^+$. $^1$H NMR (400 MHz, DMSO-d$_6$) δ: 9.50-10.50 (br m, 0.6H), 8.62 (d, J=2.9 Hz, 1H), 7.83 (td, J=8.7, 2.9 Hz, 1H), 7.65 (dd, J=8.7, 4.4 Hz, 1H), 7.52-7.60 (m, 2H), 7.43 (d, J=2.2 Hz, 1H), 7.05 (dd, J=8.7, 2.1 Hz, 1H), 6.42 (s, 1H), 6.11 (dd, J=7.5, 2.7 Hz, 1H), 6.04 (s, 2H), 5.96 (d, J=2.7 Hz, 1H), 5.21 (s, 2H), 4.20-5.00 (br m, 2H), 3.00-3.70 (br m, 6H), 2.88 (br s, 3H).

Example 10

4-(benzyloxy)-1-{3-methyl-1H,2H,3H,4H,5H-[1,4]diazepino[1,7-a]indol-9-yl}-1,2-dihydropyridin-2-one hydrochloride salt (a) Synthesis of the Free Base A mixture of 0.07 g (0.18 mmol) of 4-(benzyloxy)-1-{1H,2H,3H,4H,5H-[1,4]diazepino[1,7-a]indol-9-yl}-1,2-dihydropyridin-2-one free base [Example 3, step (b)], 5 ml of methanol, 0.132 ml (1.82 mmol) of 37% aqueous formaldehyde solution and 0.153 g (2.43 mmol) of sodium cyanoborohydride was stirred in a closed reaction vessel at 70° C. for 90 min, then at room temperature overnight. The reaction mixture was concentrated, 8 ml of saturated aqueous NaHCO$_3$ solution and 15 ml of dichloromethane were added to the residue, the phases were separated, and the water phase was extracted with 2×15 ml of dichloromethane. The combined organic phases were washed with 25 ml of brine, dried over anhydrous Na$_2$SO$_4$, filtered and concentrated in vacuum. The crude product was purified by flash column chromatography using Kieselgel 60 (0.040-0.063 mm) as adsorbent (Merck) and a 95:2:1 mixture of dichloromethane, methanol and ccNH$_4$OH as eluent, then the so obtained product was further purified by column chromatography using a 98:2:1 mixture of dichloromethane, methanol and ccNH$_4$OH as eluent to yield 0.046 g (63%) of 4-(benzyloxy)-1-{3-methyl-1H,2H,3H,4H,5H-[1,4]diazepino[1,7-a]indol-9-yl}-1,2-dihydropyridin-2-one as free base. MS (EI) 400.2 [M+H]$^+$.

(b) Synthesis of the Hydrochloride Salt 0.046 g (0.115 mmol) of 4-(benzyloxy)-1-{3-methyl-1H,2H,3H,4H,5H-[1,4]diazepino[1,7-a]indol-9-yl}-1,2-dihydropyridin-2-one free base [Example 10, step (a)] was dissolved in 10 ml of dichloromethane, 2 ml of 20% hydrogen chloride in ethyl acetate was added and the reaction mixture was concentrated. The residue was triturated with diethyl ether, the solid product was filtered, washed with diethyl ether and dried to yield 0.039 g (77%) of the title compound. MS (EI) 400.2 [M+H]$^+$. $^1$H NMR (400 MHz, DMSO-d$_6$) δ: 11.08-11.24 (br m, 1H), 7.58 (d, J=8.8 Hz, 1H), 7.54 (d, J=7.6 Hz, 1H), 7.34-7.50 (m, 6H), 7.05 (dd, J=8.8, 2.2 Hz, 1H), 6.42 (s, 1H), 6.07 (dd, J=7.4, 2.7 Hz, 1H), 5.95 (d, J=2.7 Hz, 1H), 5.14 (s, 2H), 4.83-4.94 (br m, 1H), 4.43-4.54 (br m, 1H), 3.65-3.81 (br m, 2H), 3.04-3.46 (br m, 4H), 2.89 (br d, J=4.2 Hz, 3H).

Example 11

4-[(5-chloropyridin-2-yl)methoxy]-1-{3-methyl-1H,2H,3H,4H,5H-[1,4]diazepino[1,7-a]indol-9-yl}-1,2-dihydropyridin-2-one (a) Synthesis of the Free Base To a solution of 0.3 g (0.71 mmol) of 4-[(5-chloropyridin-2-yl)methoxy]-1-{1H,2H,3H,4H,5H-[1,4]diazepino[1,7-a]indol-9-yl}-1,2-dihydropyridin-2-one free base [Example 4, step (b)] in 50 ml of acetonitrile and 25 ml of dichloromethane 0.7 ml (9.4 mmol) of 37% aqueous formaldehide solution and 0.34 g (1.6 mmol) of sodium triacetoxyborohydride were added at 0° C. The reaction mixture was stirred at room temperature overnight, 0.17 g (0.8 mmol) of sodium triacetoxyborohydride was added and the mixture was further stirred for 2.5 h. 50 ml of dichloromethane and 40 ml of 5% aqueous NaHCO$_3$ solution were added to the reaction mixture, the phases were separated, and the organic phase was washed with 2×40 ml of water and 40 ml of brine, dried over anhydrous Na$_2$SO$_4$, filtered and concentrated in vacuum. Ethanol was added to the residue and the mixture was concentrated. Ethanol addition was repeated and the solid product was filtered, washed with ethanol and dried to yield 0.067 g (21%) of the title compound. MS (EI) 435.1 [M+H]$^+$. Further 0.065 g (21%) of the title compound was obtained from the mother liquid.

(b) Synthesis of the Maleic Acid Salt

To a solution of 0.087 g (0.2 mmol) 4-[(5-chloropyridin-2-yl)methoxy]-1-{3-methyl-1H,2H,3H,4H,5H-[1,4]diazepino[1,7-a]indol-9-yl}-1,2-dihydropyridin-2-one [Example 11, step (a)], in 5 ml of dichloromethane and 2 ml of acetone 0.024 g (0.206 mmol) of maleic acid was added. The reaction mixture was concentrated in vacuum, acetone was added to the residue and the mixture was concentrated to a final volume of 0.5 ml. The solid product separated from acetone, it was filtered, washed with acetone and dried to yield 0.083 g (75%) of 4-[(5-chloropyridin-2-yl)methoxy]-1-{3-methyl-1H,2H,3H,4H,5H-[1,4]diazepino[1,7-a]indol-9-yl}-1,2-dihydropyridin-2-one maleic acid salt. MS (EI) 435.1 [M+H]$^+$. $^1$H NMR (400 MHz, DMSO-d$_6$) δ: 9.50-10.50 (br m, 0.6H), 8.67 (dd, J=2.5, 0.6 Hz, 1H), 8.03 (dd, J=8.4, 2.5 Hz, 1H), 7.53-7.63 (m, 3H), 7.43 (d, J=2.2 Hz, 1H), 7.05 (dd, J=8.7, 2.1 Hz, 1H), 6.42 (s, 1H), 6.12 (dd, J=7.5, 2.7 Hz, 1H), 6.04 (s, 2H), 5.94 (d, J=2.7 Hz, 1H), 5.22 (s, 2H), 4.20-5.00 (br m, 2H), 3.10-3.65 (br m, 6H), 2.89 (br s, 3H).

Example 12

4-[(4-chlorophenol)methoxy]-1-{3-methyl-1H,2H, 3H,4H,5H-[1,4]diazepino[1,7-a]indol-9-yl}-1,2-dihydropyridin-2-one maleic acid salt (a) Synthesis of the Free Base A mixture of 0.05 g (0.119 mmol) of 4-[(4-chlorophenyl)methoxy]-1-{1H,2H,3H,4H,5H-[1,4]diazepino[1,7-a]indol-9-yl}-1,2-dihydropyridin-2-one [Example 6, step (b)], 2.5 ml of methanol, 0.089 ml (1.19 mmol) of 370% aqueous formaldehyde solution, 0.014 ml (0.24 mmol) of acetic acid and 0.10 g (1.59 mmol) of sodium cyanoborohydride was shaken in a closed reaction vessel at 70° C. for 1 h. 7 ml of saturated aqueous $NaHCO_3$ solution and 15 ml of dichloromethane were added to the reaction mixture, the phases were separated, and the water phase was extracted with 15 ml of dichloromethane. The combined organic phases were dried over anhydrous $Na_2SO_4$, filtered and concentrated in vacuum. The crude product was purified by flash column chromatography using Kieselgel 60 (0.040-0.063 mm) adsorbent (Merck) and a 98:2:1 mixture of dichloromethane, methanol and $ccNH_4OH$ as eluent to yield 0.042 g (82%) of 4-[(4-chlorophenyl)methoxy]-1-{3-methyl-1H,2H,3H,4H, 5H-[1,4]diazepino-[1,7-a]indol-9-yl}-1,2-dihydropyridin-2-one as free base. MS (EI) 434.2 [M+H]$^+$.

(b) Synthesis of the Maleic Acid Salt

To a solution of 0.042 g (0.097 mmol) of 4-[(4-chlorophenyl)methoxy]-1-{3-methyl-1H,2H,3H,4H,5H-[1,4]diazepino[1,7-a]indol-9-yl}-1,2-dihydropyridin-2-one free base [Example 12, step (a)] in 10 ml of a 9:1 mixture of dichloromethane and ethanol 0.011 g (0.095 mmol) of maleic acid was added, then the dichloromethane was evaporated in vacuum. Diethyl ether was added to the residue, the solid product was filtered, washed with diethyl ether and dried to yield 0.039 g (74%) of the title compound. MS (EI) 434.1 [M+H]$^+$. $^1$H NMR (400 MHz, DMSO-d$_6$) δ: 7.57 (d, J=8.8 Hz, 1H), 7.53 (d, J=7.6 Hz, 1H), 7.50 (s, 4H), 7.43 (d, J=2.0 Hz, 1H), 7.05 (dd, J=8.7, 2.1 Hz, 1H), 6.41 (s, 1H), 6.08 (dd, J=7.5, 2.7 Hz, 1H), 6.04 (s, 2H), 5.94 (d, J=2.7 Hz, 1H), 5.15 (s, 2H), 4.25-4.90 (br m, 2H), 3.00-3.75 (br m, 6H), 2.88 (br s, 3H).

Example 13

4-[(2-fluorophenyl)methoxy]-1-{3-methyl-1H,2H, 3H,4H,5H-[1,4]diazepino[1,7-a]indol-9-yl}-1,2-dihydropyridin-2-one hydrochloride salt (a) Synthesis of the Free Base The free base form of 4-[(2-fluorophenyl)methoxy]-1-{3-methyl-1H,2H,3H,4H,5H-[1,4]diazepino[1,7-a]indol-9-yl}-1,2-dihydropyridin-2-one was obtained from 1-{1H,2H,3H,4H,5H-[1,4]diazepino[1,7-a]indol-9-yl}-4-[(2-fluorophenyl)methoxy]-1,2-dihydropyridin-2-one [Example 7, step (b)] according to the method described in step (a) of Example 12. MS (EI) 418.2 [M+H]$^+$.

(b) Synthesis of the Hydrochloride Salt

To a solution of 0.042 g (0.10 mmol) of 4-[(2-fluorophenyl)methoxy]-1-{3-methyl-1H,2H,3H,4H,5H-[1,4]diazepino[1,7-a]indol-9-yl}-1,2-dihydropyridin-2-one free base [Example 13, step (a)] in 10 ml of a 9:1 mixture of dichloromethane and ethanol 1 ml of 20% hydrogen chloride in ethyl acetate was added, and the reaction mixture was concentrated. The residue was triturated with diethyl ether, the solid product was filtered, washed with diethyl ether and dried to yield 0.030 g (66%) of the title compound. MS (EI) 418.2 [M+H]$^+$. $^1$H NMR (400 MHz, DMSO-d$_6$) δ: 10.98-11.16 (br m, 1H), 7.51-7.63 (m, 3H), 7.42-7.51 (m, 2H), 7.25-7.33 (m, 2H), 7.06 (dd, J=8.7, 2.1 Hz, 1H), 6.42 (s, 1H), 6.06 (dd, J=7.5, 2.7 Hz, 1H), 6.02 (d, J=2.7 Hz, 1H), 5.17 (s, 2H), 4.80-4.99 (br m, 1H), 4.38-4.60 (br m, 1H), 3.60-3.83 (br m, 2H), 3.00-3.46 (br m, 4H), 2.89 (br s, 3H).

Example 14

1-{3-ethyl-1H,2H,3H,4H,5H-[1,4]diazepino[1,7-a]indol-9-yl}-4-[(4-methoxyphenyl)methoxy]-1,2-dihydropyridin-2-one To a solution of 0.177 g (0.22 mmol) of 1-{1H,2H,3H, 4H,5H-[1,4]diazepino[1,7-a]indol-9-yl}-4-[(4-methoxyphenyl)methoxy]-1,2-dihydropyridin-2-one [Example 2, step (b)] in 20 ml of dichloromethane 0.03 ml (0.53 mmol) of acetaldehyde was added, then 0.11 g (0.52 mmol) of sodium triacetoxyborohydride was added at 0° C. and the reaction mixture was stirred at room temperature overnight. 30 ml of dichloromethane and 25 ml of saturated aqueous $NaHCO_3$ solution were added to the reaction mixture, the phases were separated, the organic phase was washed with 2×40 ml of water, dried over anhydrous $Na_2SO_4$, filtered and concentrated in vacuum. The crude product was purified by column chromatography using Kieselgel 60 (0.040-0.063 mm) as adsorbent (Merck) and a 95:5 mixture of dichloromethane and methanol as eluent. The obtained product was triturated with diethyl ether, filtered, washed with diethyl ether and dried to yield 0.024 g (25%) of the title compound. MS (EI) 444.3 [M+H]$^+$.

Example 15

4-[(5-chloropyridin-2-yl)methoxy]-1-{3-etil-1H,2H, 3H,4H,5H-[1,4]diazepino[1,7-a]indol-9-yl}-1,2-dihydropyridin-2-one (a) Synthesis of the Free Base To a solution of 0.3 g (0.71 mmol) of 4-[(5-chloropyridin-2-yl)methoxy]-1-{1H,2H,3H,4H,5H-[1,4]diazepino[1,7-a]indol-9-yl}-1,2-dihydropyridin-2-one [Example 4, step (b)] in 50 ml of dichloromethane 0.08 ml (1.4 mmol) of acetaldehyde was added at 0° C. and the reaction mixture was stirred at this temperature for 10 min. Then 0.33 g (1.56 mmol) of sodium triacetoxyborohydride was added at 0° C., and the reaction mixture was stirred at room temperature overnight. 40 ml of 5% aqueous $NaHCO_3$ solution was added to the reaction mixture, the phases were separated, the organic phase was washed with 2×40 ml of water, dried over anhydrous $Na_2SO_4$, filtered and concentrated in vacuum. The crude product was purified by column chromatography using Kieselgel 60 (0.040-0.063 mm) as adsorbent (Merck) and a 9:1 mixture of dichloromethane and methanol as eluent. The obtained solid product was triturated with ethanol and diethyl ether, filtered, washed with diethyl ether and dried to yield 0.144 g (45%) of the title compound. MS (EI) 449.2 [M+H]$^+$.

(b) Synthesis of the Maleic Acid Salt

To a solution of 0.10 g (0.23 mmol) of 4-[(5-chloropyridin-2-yl)methoxy]-1-{3-ethyl-1H,2H,3H,4H,5H-[1,4]diazepino[1,7-a]indol-9-yl}-1,2-dihydropyridin-2-one [Example 15, step (a)] in 5 ml of dichloromethane and 2 ml of acetone 0.027 g (0.233 mmol) of maleic acid was added. The reaction mixture was concentrated in vacuum acetone was added to the residue and the mixture was concentrated to a final volume of 0.5 ml. The solid product separated from acetone, it was filtered, washed with acetone and dried to yield 0.116 g (89%) of 4-[(5-chloropyridin-2-yl)methoxy]-1-{3-ethyl-1H,2H,3H,4H,5H-[1,4]diazepino[1,7-a]indol-9-yl}-1,2-dihydropyridin-2-one maleic acid salt. MS (EI) 449.15 [M+H]$^+$. $^1$H NMR (400 MHz, DMSO-d$_6$) δ: 9.30-10.00 (br m, 0.7H), 8.67 (dd, J=2.5, 0.7 Hz, 1H), 8.03 (dd, J=8.4, 2.5 Hz, 1H), 7.53-7.63 (m, 3H), 7.43 (d, J=2.2 Hz, 1H), 7.05 (dd, J=8.7, 2.1 Hz, 1H), 6.43 (s, 1H), 6.12 (dd, J=7.5, 2.7 Hz, 1H), 6.04 (s, 2H), 5.94 (d, J=2.7 Hz, 1H), 5.22 (s, 2H), 5.10-4.20 (br m, 2H), 2.90-4.00 (br m, 8H), 1.26 (t, J=7.1 Hz, 3H).

Example 16

1-{3-ethyl-1H,2H,3H,4H,5H-[1,4]diazepino[1,7-a]indol-9-yl}-4-[(4-fluorophenyl)methoxy]-1,2-dihydropyridin-2-one To a solution of 0.097 g (0.24 mmol) of 1-{1H,2H,3H,4H,5H-[1,4]diazepino[1,7-a]indol-9-yl}-4-[(4-fluorophenyl)methoxy]-1,2-dihydropyridin-2-one [Example 5, step (a)] in 20 ml of dichloromethane 0.03 ml (0.53 mmol) of acetaldehyde was added at 0° C. and the reaction mixture was stirred at this temperature for 10 min. Then 0.11 g (0.52 mmol) of sodium triacetoxyborohydride was added at 0° C. and the reaction mixture was stirred at room temperature overnight. 20 ml of dichloromethane and 40 ml of 10% aqueous NaHCO$_3$ solution were added to the reaction mixture, the phases were separated, the organic phase was washed with 2×30 ml of water, dried over anhydrous Na$_2$SO$_4$, filtered and concentrated in vacuum. The crude product was purified by column chromatography using Kieselgel 60 (0.040-0.063 mm) as adsorbent (Merck) and a 95:5 mixture of dichloromethane and methanol as eluent. The obtained product was triturated with diethyl ether, filtered, washed with diethyl ether and dried to yield 0.022 g (21%) of the title compound. MS (EI) 432.29 [M+H]$^+$.

Example 17

1-{3-acetyl-1H,2H,3H,4H,5H-[1,4]diazepino[1,7-a]indol-9-yl}-4-[(5-chloropyridin-2-yl)methoxy]-1,2-dihydropyridin-2-one To a solution of 0.3 g (0.71 mmol) of 4-[(5-chloropyridin-2-yl)methoxy]-1-{1H,2H,3H,4H,5H-[1,4]diazepino[1,7-a]indol-9-yl}-1,2-dihydropyridin-2-one [Example 4, step (b)] in 50 ml of dichloromethane 0.2 ml (1.4 mmol) of triethylamine and 0.08 ml (1.12 mmol) of acetic anhydride were added below 10° C. The reaction mixture was stirred at room temperature overnight, 25 ml of dichloromethane was added and the organic phase was washed with 3×40 ml of water. The organic phase was dried over anhydrous Na$_2$SO$_4$, filtered and concentrated in vacuum. The residue was triturated with ethanol, filtered, washed with ethanol and diethyl ether, and dried to yield 0.21 g (63%) of the title compound. MS (EI) 463.2 [M+H]$^+$.

Example 18

4-[(5-fluoropyridin-2-yl)methoxy]-1-[3-(propan-2-yl)-1H,2H,3H,4H,5H-[1,4]diazepino[1,7-a]indol-9-yl]-1,2-dihydropyridin-2-one maleic acid salt (a) Synthesis of the Free Base
A mixture of 0.11 g (0.27 mmol) of 1-{1H,2H,3H,4H,5H-[1,4]diazepino[1,7-a]indol-9-yl}-4-[(5-fluoropyridin-2-yl)methoxy]-1,2-dihydropyridin-2-one [Example 1, step (a)], 10 ml of methanol, 0.73 ml (9.94 mmol) of acetone, 0.028 ml (0.45 mmol) of acetic acid and 0.21 g (3.34 mmol) of sodium cyanoborohydride was stirred in a closed reaction vessel at 70° C. for 6.25 h, then 20 ml of saturated aqueous NaHCO$_3$ solution was added and the reaction mixture was stirred at room temperature overnight. The reaction mixture was extracted with 3×20 ml of dichloromethane, the combined organic phases were dried over anhydrous Na$_2$SO$_4$, filtered and concentrated in vacuum. The crude product was purified by flash column chromatography using Kieselgel 60 (0.040-0.063 mm) as adsorbent (Merck) and a 98:2:1 mixture of dichloromethane, methanol and ccNH$_4$OH as eluent to yield 0.068 g (56%) of 4-[(5-fluoropyridin-2-yl)methoxy]-1-[3-(propan-2-yl)-1H,2H,3H,4H,5H-[1,4]diazepino[1,7-a]indol-9-yl]-1,2-dihydropyridin-2-one as free base. MS (EI) 447.2 [M+H]$^+$.

(b) Synthesis of the Maleic Acid Salt
To a solution of 0.037 g (0.084 mmol) of 4-[(5-fluoropyridin-2-yl)methoxy]-1-[3-(propan-2-yl)-1H,2H,3H,4H,5H-[1,4]diazepino[1,7-a]indol-9-yl]-1,2-dihydropyridin-2-one free base [Example 18, step (a)] in a 9:1 mixture of dichloromethane and ethanol 0.01 g (0.084 mmol) of maleic acid was added, then the reaction mixture was concentrated. The residue was triturated with diethyl ether, the solid product was filtered, washed with diethyl ether and dried to yield 0.043 g (90%) of the title compound. MS (EI) 447.2 [M+H]$^+$. $^1$H NMR (400 MHz, DMSO-d$_6$) δ: 9.20-10.10 (br m, 0.7H), 8.62 (br d, J=2.9 Hz, 1H), 7.83 (td, J=8.7, 3.0 Hz, 1H), 7.65 (dd, J=8.7, 4.4 Hz, 1H), 7.51-7.58 (m, 2H), 7.44 (d, J=2.0 Hz, 1H), 7.06 (dd, J=8.8, 2.2 Hz, 1H), 6.44 (s, 1H), 6.11 (dd, J=7.6, 2.7 Hz, 1H), 6.05 (s, 2H), 5.95 (d, J=2.9 Hz, 1H), 5.21 (s, 2H), 4.20-5.10 (br m, 2H), 2.90-3.90 (br m, 7H), 1.26 (br d, J=6.6 Hz, 6H).

Example 19

4-(benzyloxy)-1-[3-(propan-2-yl)-1H,2H,3H,4H,5H-[1,4]diazepino[1,7-a]indol-9-yl]-1,2-dihydropyridin-2-one hydrochloride salt (a) Synthesis of the Free Base
A mixture of 0.07 g (0.18 mmol) of 4-(benzyloxy)-1-{1H,2H,3H,4H,5H-[1,4]diazepino[1,7-a]indol-9-yl}-1,2-dihydropyridin-2-one [Example 3, step (b)], 5 ml of methanol, 0.53 ml (7.2 mmol) of acetone, 0.011 ml (0.19 mmol) of acetic acid and 0.153 g (2.43 mmol) of sodium cyanoborohydride was stirred in a closed reaction vessel at 75° C. for 4.25 h, then at room temperature overnight. 0.039 g (0.62 mmol) of sodium cyanoborohydride was added and the reaction mixture was stirred at 75° C. for 24 h. 10 ml of saturated aqueous NaHCO$_3$ solution was added and the reaction mixture was extracted with 3×15 ml of dichloromethane, the combined organic phases were washed with water, and brine, dried over anhydrous Na$_2$SO$_4$, filtered and concentrated in vacuum to yield 0.073 g (95%) of 4-(benzyloxy)-1-[3-(propan-2-yl)-1H,2H,3H,4H,5H-[1,4]diazepino[1,7-a]indol-9-yl]-1,2-dihydropyridin-2-one as free base. MS (EI) 428.2 [M+H]$^+$.

(b) Synthesis of the Maleic Acid Salt
To a solution of 0.0326 g (0.076 mmol) of 4-(benzyloxy)-1-[3-(propan-2-yl)-1H,2H,3H,4H,5H-[1,4]diazepino[1,7-a]indol-9-yl]-1,2-dihydropyridin-2-one free base [Example 19, step (a)] in 2 ml of a 9:1 mixture of dichloromethane and ethanol 0.0089 g (0.076 mmol) of maleic acid was added, then the dichlorormethane was evaporated. The residue was triturated with diethyl ether, the solid product was filtered, washed with diethyl ether and dried to yield 0.039 g (94%) of 4-(benzyloxy)-1-[3-(propan-2-yl)-1H,2H,3H,4H,5H-[1,4]diazepino[1,7-a]indol-9-yl]-1,2-dihydropyridin-2-one maleic acid salt. MS (EI) 428.2 [M+H]$^+$. $^1$H NMR (400 MHz, DMSO-d$_6$) δ: 9.20-9.90 (br m, 0.6H), 7.50-7.58 (m, 2H), 7.34-7.50 (m, 6H), 7.05 (dd, J=8.8, 2.2 Hz, 1H), 6.43 (s, 1H), 6.08 (dd, J=7.5, 2.6 Hz, 1H), 6.04 (s, 2H), 5.95 (d, J=2.6 Hz, 1H), 5.14 (s, 2H), 4.20-5.00 (br m, 2H), 2.90-3.90 (br m, 7H), 1.25 (br d, J=5.9 Hz, 6H).

(c) Synthesis of the Hydrochloride Salt 0,073 g (0.17 mmol) of 4-(benzyloxy)-1-[3-(propan-2-yl)-1H,2H,3H,4H,5H-[1,4]diazepino[1,7-a]indol-9-yl]-1,2-dihydropyridin-2-one free base [Example 19, step (a)] was taken up in 10 ml of dichloromethane and 10 ml of methanol. 5 ml of 200/% hydrogen chloride in ethyl acetate was added, the reaction mixture was filtered and the solution was evaporated. The residue was triturated with 4 ml of a 3:1 mixture of ethanol and diethyl ether, the solid product was filtered, washed with diethyl ether and dried to yield 0,061 g (77%) of 4-(benzyloxy)-1-[3-(propan-2-yl)-1H,2H,3H,4H,5H-[1,4]diazepino[1,7-a]indol-9-yl]-1,2-dihydropyridin-2-one hydrochloride salt. MS (EI) 428.2 [M+H]+.

Example 20

4-[(5-chloropyridin-2-yl)methoxy]-1-[3-(propan-2-yl)-1H,2H,3H,4H,5H-[1,4]diazepino[1,7-a]indol-9-yl]-1,2-dihydropyridin-2-one maleic acid salt (a) Synthesis of the Free Base A mixture of 0.57 g (1.36 mmol) of 4-[(5-chloropyridin-2-yl)methoxy]-1-{1H,2H,3H,4H,5H-[1,4]diazepino[1,7-a]indol-9-yl}-1,2-dihydropyridin-2-one [Example 4, step (b)], 60 ml acetonitrile, 0.38 g (2.72 mmol) of K$_2$CO$_3$ and 1.36 ml (13.6 mmol) of 2-iodopropane was stirred at reflux temperature for 45 h. The reaction mixture was concentrated, the residue was triturated with 20 ml of water, the solid product was filtered and washed with water. The crude product was purified by column chromatography using Kieselgel 60 (0.040-0.063 mm) as adsorbent (Merck) and a 95:5:0.1 mixture of dichloromethane, methanol and ccNH$_4$OH as eluent to yield 0.4 g (64%) of 4-[(5-chloropyridin-2-yl)methoxy]-1-[3-(propan-2-yl)-1H,2H,3H,4H,5H-[1,4]diazepino[1,7-a]indol-9-yl]-1,2-dihydropyridin-2-one as free base. MS (EI) 463.2 [M+H]$^+$.

(b) Synthesis of the Maleic Acid Salt

To a solution of 0.47 g (1.015 mmol) of 4-[(5-chloropyridin-2-yl)methoxy]-1-[3-(propan-2-yl)-1H,2H,3H,4H,5H-[1,4]diazepino[1,7-a]indol-9-yl]-2-dihydropyridin-2-one free base [Example 20, step (a)] in a 10:1 mixture of dichloromethane and methanol 0.13 g (1.117 mmol) of maleic acid was added and the mixture was concentrated. The residue was triturated with ethanol, and after 1 h stirring the solid product was filtered, washed with ethanol and dried to yield 0.57 g (96%) of the title compound. MS (EI) 463.2 [M+H]$^+$. $^1$H NMR (500 MHz, DMSO-d$_6$) δ: 9.00-10.00 (br m, 0.5H), 8.67 (br d, J=2.4 Hz, 1H), 8.03 (dd, J=8.4, 2.5 Hz, 1H), 7.61 (d, J=8.4 Hz, 1H), 7.53-7.58 (m, 2H), 7.44 (d, J=2.0 Hz, 1H), 7.05 (dd, J=8.7, 2.0 Hz, 1H), 6.43 (s, 1H), 6.12 (dd, J=7.6, 2.8 Hz, 1H), 6.05 (s, 2H), 5.93 (d, J=2.8 Hz, 1H), 5.23 (s, 2H), 4.10-5.10 (br m, 2H), 2.70-4.00 (br m, 7H), 1.26 (br d, J=6.7 Hz, 6H).

Example 21

4-[(4-fluorophenyl)methoxy]-1-[3-(propan-2-yl)-1H,2H,3H,4H,5H-[1,4]diazepino[1,7-a]indol-9-yl]-1,2-dihydropyridin-2-one To a solution of 0.060 g (0.15 mmol) of 1-{1H,2H,3H,4H,5H-[1,4]diazepino[1,7-a]indol-9-yl}-4-[(4-fluorophenyl)methoxy]-1,2-dihydropyridin-2-one [Example 5, step (a)], 20 ml of dichloromethane, 0.2 ml (1.43 mmol) of triethylamine and 0.04 ml (0.545 mmol) of acetone 0.1 g (0.47 mmol) of sodium triacetoxyborohydride was added at 0° C. and the reaction mixture was stirred at room temperature overnight. 0.02 ml (0.27 mmol) of acetone and 0.050 g (2.35 mmol) of sodium cyanoborohydride were added and the reaction mixture was stirred at room temperature for 24 h. After this further 0.02 ml (0.27 mmol) of acetone and 0.050 g (2.36 mmol) of sodium triacetoxyborohydride were added and the reaction mixture was stirred for further 24 h. 40 ml of dichloromethane and 10 ml of saturated aqueous NaHCO$_3$ solution were added and the reaction mixture was stirred for 10 min. The phases were separated, the organic phase was washed with 2×30 ml of water, dried over anhydrous Na$_2$SO$_4$, filtered and concentrated in vacuum. The crude product was purified by column chromatography using Kieselgel 60 (0.040-0.063 mm) as adsorbent (Merck) and a 9:1 mixture of dichloromethane and methanol as eluent. The obtained product was crystallized with ethanol, the precipitated solid product was filtered, washed with diethyl ether and dried. The so obtained product and the concentrated mother liquid were purified together (0.046 g) by column chromatography using Kieselgel 60 (0.040-0.063 mm) as adsorbent (Merck) and a 95:5 mixture of dichloromethane and methanol as eluent to yield 0.021 g (31%) of the title compound. MS (EI) 446.25 [M+H]$^+$.

Example 22

4-[(4-chlorophenyl)methoxy]-1-[3-(propan-2-yl)-1H,2H,3H,4H,5H-[1,4]diazepino[1,7-a]indol-9-yl]-1,2-dihydropyridin-2-one maleic acid salt (a) Synthesis of the Free Base A mixture of 0.070 g (0.167 mmol) of 4-[(4-chlorophenyl)methoxy]-1-{1H,2H,3H,4H,5H-[1,4]diazepino[1,7-a]indol-9-yl}-1,2-dihydropyridin-2-one free base [Example 6, step (b)], 6 ml of methanol, 0.49 ml (6.67 mmol) of acetone and 0.142 g (2.26 mmol) of sodium cyanoborohydride was stirred in a closed reaction vessel at 70° C. overnight. 6 ml of methanol and 15 ml of saturated aqueous NaHCO$_3$ solution were added and the reaction mixture was stirred at room temperature for 3 h. The reaction mixture was extracted with 3×20 ml of dichloromethane, the combined organic phases were dried over anhydrous Na$_2$SO$_4$, filtered and concentrated in vacuum. The crude product was purified by flash column chromatography using Kieselgel 60 (0.040-0.063 mm) as adsorbent (Merck) and a 95:5:1 mixture of dichloromethane, methanol and ccNH$_4$OH as eluent to yield 0.065 g (84%) of 4-[(4-chlorophenyl)methoxy]-1-[3-(propan-2-yl)-1H,2H,3H,4H,5H-[1,4]diazepino[1,7-a]indol-9-yl]-1,2-dihydropyridin-2-one as free base. MS (EI) 462.2 [M+H]$^+$.

(b) Synthesis of the Maleic Acid Salt

To a solution of 0.065 g (0.14 mmol) of 4-[(4-chlorophenyl)methoxy]-1-[3-(propan-2-yl)-1H,2H,3H,4H,5H-[1,4]diazepino[1,7-a]indol-9-yl]-1,2-dihydropyridin-2-one free base [Example 22, step (a)] in 10 ml of a 9:1 mixture of dichloromethane and ethanol 0.0164 g (0.14 mmol) of maleic acid was added, then the dichlorormethane was evaporated. The residue was triturated with diethyl ether, the solid product was filtered, washed with diethyl ether and dried to yield 0.066 g (81%) of the title compound. MS (EI) 462.2 [M+H]$^+$. $^1$H NMR (400 MHz, DMSO-d$_6$) δ: 9.00-10.00 (br m, 0.7H), 7.48-7.58 (m, 6H), 7.43 (d, J=1.9 Hz, 1H), 7.05 (dd, J=8.7, 2.0 Hz, 1H), 6.44 (s, 1H), 6.03-6.11 (m, 3.3H), 5.94 (d, J=2.7 Hz, 1H), 5.15 (s, 2H), 4.20-5.05 (br m, 2H), 2.90-3.90 (br m, 7H), 1.18-1.34 (br d, J=6.4 Hz, 6H).

Example 23

4-[(2-fluorophenyl)methoxy]-1-[3-(propan-2-yl)-1H,2H,3H,4H,5H-[1,4]diazepino[1,7-a]indol-9-yl]-1,2-dihydropyridin-2-one hydrochloride salt (a) Synthesis of the Free Base A mixture of 0.070 g (0.174 mmol) of 1-{1H,2H,3H,4H,5H-[1,4]diazepino[1,7-a]indol-9-yl}-4-[(2-fluorophenyl)methoxy]-1,2-dihydropyridin-2-one [Example 7, step (b)], 5 ml of methanol, 0.51 ml (6.95 mmol) of acetone, 0.02 ml (0.35 mmol) of acetic acid and 0.21 g (3.34 mmol) of sodium cyanoborohydride was stirred in a closed reaction vessel at 70° C. for 6.25 h. 15 ml of saturated aqueous NaHCO$_3$ solution was added and the reaction mixture was stirred at room temperature overnight. The reaction mixture was extracted with 3×15 ml of dichloromethane, the combined organic phases were dried over anhydrous Na$_2$SO$_4$, filtered and concentrated in vacuum. The crude product was purified by flash column chromatography using Kieselgel 60 (0.040-0.063 mm) as adsorbent (Merck) and a 98:2:1 mixture of dichloromethane, methanol and ccNH$_4$OH as eluent to yield 0.030 g (38%) of 4-[(2-fluorophenyl)methoxy]-1-[3-(propan-2-yl)-1H,2H,3H,4H,5H-[1,4]diazepino[1,7-a]indol-9-yl]-1,2-dihydropyridin-2-one as free base. MS (EI) 446.2 [M+H]$^+$.

(b) Synthesis of the Hydrochloride Salt

To a solution of 0.030 g (0.067 mmol) of 4-[(2-fluorophenyl)methoxy]-1-[3-(propan-2-yl)-1H,2H,3H,4H,5H-[1,4]diazepino[1,7-a]indol-9-yl]-1,2-dihydropyridin-2-one [Example 23, step (a)] in 8 ml of dichloromethane 1 ml of 20%° hydrogen chloride in ethyl acetate was added and the reaction mixture was concentrated. The residue was triturated with diethyl ether, the solid product was filtered, washed with diethyl ether and dried to yield 0.025 g (77%) of the title compound. MS (EI) 446.2 [M+H]$^+$. $^1$H NMR (400 MHz, DMSO-d$_6$) δ: 10.69-10.84 (br m, 1H), 7.42-7.62 (m, 5H), 7.24-7.33 (m, 2H), 7.06 (dd, J=8.7, 2.1 Hz, 1H), 6.44 (s, 1H), 6.06 (dd, J=7.5, 2.7 Hz, 1H), 6.01 (d, J=2.7 Hz, 1H), 5.17 (s, 2H), 4.85-4.95 (br m, 1H), 4.56-4.67 (br m, 1H), 3.67-3.80 (br m, 3H), 3.50-3.61 (br m, 1H), 3.20-3.49 (br m, 2H), 2.99-3.10 (br m, 1H), 1.26-1.34 (m, 6H).

Example 24

1-[11-chloro-3-(propan-2-yl)-1H,2H,3H,4H,5H-[1,4]diazepino[1,7-a]indol-9-yl]-4-[(5-chloropyridin-2-yl)methoxy]-1,2-dihydropyridin-2-one maleic acid salt (a) Synthesis of the Free Base To a solution of 0.20 g (0.43 mmol) of 4-[(5-chloropyridin-2-yl)methoxy]-1-[3-(propan-2-yl)-1H,2H,3H,4H,5H-[1,4]diazepino[1,7-a]indol-9-yl]-1,2-dihydropyridin-2-one [Example 20, step (a)] in 2 ml of dichloromethane 0.064 g (0.48 mmol) of N-chlorosuccinimide was added and the reaction mixture was stirred at room temperature for 45 min. The reaction mixture was concentrated and the residue was purified by flash column chromatography using Kieselgel 60 (0.040-0.063 mm) as adsorbent (Merck) and different mixtures of dichloromethane and methanol as eluent: first a 98:2, then a 97:3, and finally a 95:5 mixture to yield 0.146 g (67%) of 1-[11-chloro-3-(propan-2-yl)-1H,2H,3H,4H,5H-[1,4]diazepino[1,7-a]indol-9-yl]-4-[(5-chloropyridin-2-yl)methoxy]-1,2-dihydropyridin-2-one as free base. MS (EI) 497.1 [M+H]$^+$.

(b) Synthesis of the Maleic Acid Salt

To a solution of 0.1 g (0.2 mmol) of 1-[11-chloro-3-(propan-2-yl)-1H,2H,3H,4H,5H-[1,4]diazepino[1,7-a]indol-9-yl]-4-[(5-chloro-pyridin-2-yl)methoxy]-1,2-dihydropyridin-2-one free base [Example 24, step (a)] in 3 ml of a 9:1 mixture of dichloromethane and ethanol 0.0233 g (0.2 mmol) of maleic acid was added, then the dichlorormethane was evaporated in vacuum. The residue was triturated with diethyl ether, the solid product was filtered, washed with diethyl ether and dried to yield 0.104 g (84%) of the title compound. MS (EI) 497.2 [M+H]$^+$. $^1$H NMR (400 MHz, DMSO-d$_6$) δ: 9.00-10.20 (br m, 0.7H) 8.68 (dd, J=2.5, 0.6 Hz, 1H), 8.03 (dd, J=8.4, 2.5 Hz, 1H), 7.67 (d, J=8.9 Hz, 1H), 7.56-7.64 (m, 2H), 7.39 (d, J=2.0 Hz, 1H), 7.18 (dd, J=8.7, 2.1 Hz, 1H), 6.14 (dd, J=7.6, 2.7 Hz, 1H), 6.04 (s, 1.86H), 5.95 (d, J=2.7 Hz, 1H), 5.23 (s, 2H), 5.10-4.20 (br m, 2H), 2.85-4.00 (br m, 7H), 1.12-1.32 (br d, 6H).

Example 25

1-[11-bromo-3-(propan-2-yl)-1H,2H,3H,4H,5H-[1,4]diazepino[1,7-a]indol-9-yl]-4-[(5-chloropyridin-2-yl)methoxy]-1,2-dihydropyridin-2-one maleic acid salt (a) Synthesis of the Free Base To a solution of 0.20 g (0.43 mmol) of 4-[(5-chloropyridin-2-yl)methoxy]-1-[3-(propan-2-yl)-1H,2H,3H,4H,5H-[1,4]diazepino[1,7-a]indol-9-yl]-1,2-dihydropyridin-2-one [Example 20, step (a)] in 4 ml of dichloromethane 0.089 g (0.5 mmol) of N-bromosuccinimide was added and the reaction mixture was stirred at room temperature for 75 min. 40 ml dichloromethane and 10 ml of 1N aqueous NaOH solution were added. The mixture was stirred at room temperature for 1 h, then the phases were separated. The organic phase was washed with 2×10 ml of 1N aqueous NaOH solution, water and brine, then dried over anhydrous Na$_2$SO$_4$, filtered and concentrated in vacuum. The residue was purified by flash column chromatography using Kieselgel 60 (0.040-0.063 mm) as adsorbent (Merck) and a 98:2 mixture of dichloromethane and methanol as eluent. The so obtained solid product was triturated with diethyl ether, filtered, washed with diethyl ether and dried to yield 0.056 g (24%) of the title compound 1-[11-bromo-3-(propan-2-yl)-1H,2H,3H,4H,5H-[1,4]diazepino[1,7-a]indol-9-yl]-4-[(5-chloropyridin-2-yl)methoxy]-1,2-dihydropyridin-2-one as free base. MS (EI) 543.1 [M+H]$^+$.

(b) Synthesis of the Maleic Acid Salt

To a solution of 0.037 g (0.068 mmol) of 1-[11-bromo-3-(propan-2-yl)-1H,2H,3H,4H,5H-[1,4]diazepino[1,7-a]indol-9-yl]-4-[(5-chloropyridin-2-yl)methoxy]-1,2-dihydropyridin-2-one [Example 25, step (a)] in 2 ml of a 9:1 mixture of dichloromethane and ethanol 0.0079 g (0.068 mmol) of maleic acid was added, then the dichlorormethane was evaporated in vacuum. The residue was triturated with diethyl ether, the solid product was filtered, washed with diethyl ether and dried to yield 0.038 g (83%) of the title compound. MS (EI) 543.1 [M+H]$^+$. $^1$H NMR (400 MHz, DMSO-d$_6$) δ: 9.10-10.00 (br m, 0.6H), 8.68 (dd, J=2.5, 0.6 Hz, 1H), 8.03 (dd, J=8.3, 2.4 Hz, 1H), 7.67 (d, J=8.8 Hz, 1H), 7.56-7.64 (m, 2H), 7.31 (d, J=2.0 Hz, 1H), 7.17 (dd, J=8.7, 2.1 Hz, 1H), 6.14 (dd, J=7.6, 2.7 Hz, 1H), 6.04 (s, 1.8H), 5.95 (d, J=2.7 Hz, 1H), 5.23 (s, 2H), 4.15-5.10 (br m, 2H), 2.80-4.00 (br m, 7H), 1.15-1.30 (br d, 6H).

Example 26

4-[(5-chloropyridin-2-yl)methoxy]-1-[11-iodo-3-(propan-2-yl)-1H,2H,3H,4H,5H-[1,4]diazepino[1,7-a]indol-9-yl]-1,2-dihydropyridin-2-one maleic acid salt (a) Synthesis of the Free Base To a solution of 0.20 g (0.43 mmol) of 4-[(5-chloropyridin-2-yl)methoxy]-1-[3-(propan-2-yl)-1H,2H,3H,4H,5H-[1,4]diazepino[1,7-a]indol-9-yl]-1,2-dihydropyridin-2-one [Example 20, step (a)] in 4 ml of dichloromethane 0.113 g (0.5 mmol) of N-iodosuccinimide was added and the reaction mixture was stirred at room temperature for 1 h. 40 ml dichloromethane and 10 ml of 1N aqueous NaOH solution were added. The mixture was stirred at room temperature for 1 h, then the phases were separated. The organic phase was washed with 2×10 ml of 1N aqueous NaOH solution, water and brine, then dried over anhydrous $Na_2SO_4$, filtered and concentrated in vacuum. The residue was purified by flash column chromatography using Kieselgel 60 (0.040-0.063 mm) as adsorbent (Merck) and a 95:5 mixture of dichloromethane and methanol as eluent to yield 0.171 g (67%) of 4-[(5-chloropyridin-2-yl)methoxy]-1-[11-iodo-3-(propan-2-yl)-1H,2H,3H,4H,5H-[1,4]diazepino[1,7-a]indol-9-yl]-1,2-dihydropyridin-2-one as free base. MS (EI) 589.1 $[M+H]^+$.

(b) Synthesis of the Maleic Acid Salt

To a solution of 0.040 g (0.068 mmol) of 4-[(5-chloropyridin-2-yl)methoxy]-1-[11-iodo-3-(propan-2-yl)-1H,2H,3H,4H,5H-[1,4]diazepino[1,7-a]indol-9-yl]-1,2-dihydropyridin-2-one [Example 26, step (a)] in 1.2 ml of a 9:1 mixture of dichloromethane and ethanol 0.0079 g (0.068 mmol) of maleic acid was added, then the reaction mixture was concentrated in vacuum. The residue was triturated with diethyl ether, the solid product was filtered, washed with diethyl ether and dried to yield 0.026 g (63%) of the title compound. MS (EI) 589.1 $[M+H]^+$. $^1H$ NMR (400 MHz, DMSO-$d_6$) δ: 9.20-10.00 (br m, 0.5H), 8.68 (dd, J=2.5, 0.6 Hz, 1H), 8.03 (dd, J=8.2, 2.5 Hz, 1H), 7.56-7.64 (m, 3H), 7.10-7.19 (m, 2H), 6.14 (dd, J=7.6, 2.7 Hz, 1H), 6.03 (s, 1.34H), 5.95 (d, J=2.7 Hz, 1H), 5.24 (s, 2H), 4.25-5.15 (br m, 2H), 2.70-4.00 (m, 7H), 0.90-1.40 (br d, 6H).

Example 27

4-(benzyloxy)-1-[11-chloro-3-(propan-2-yl)-1H,2H,3H,4H,5H-[1,4]diazepino[1,7-a]indol-9-yl]-1,2-dihydropyridin-2-one hydrochloride salt (a) Synthesis of the Free Base To a solution of 0.073 g (0.17 mmol) of 4-(benzyloxy)-1-[3-(propan-2-yl)-1H,2H,3H,4H,5H-[1,4]diazepino[1,7-a]indol-9-yl]-1,2-dihydropyridin-2-one [Example 19, step (a)] in 2 ml of dichloromethane 0.024 g (0.18 mmol) of N-chlorosuccinimide was added and the reaction mixture was stirred at room temperature for 70 min. 20 ml dichloromethane and 5 ml of 1N aqueous NaOH solution were added. The mixture was stirred at room temperature for 1 h, then the phases were separated. The organic phase was washed with 2×5 ml of 1N aqueous NaOH solution, water and brine, then dried over anhydrous $Na_2SO_4$, filtered and concentrated in vacuum. The residue was purified by flash column chromatography using Kieselgel 60 (0.040-0.063 mm) as adsorbent (Merck) and a 98:2 mixture of dichloromethane and methanol as eluent to yield 0.038 g (48%) of 4-(benzyloxy)-1-[11-chloro-3-(propan-2-yl)-1H,2H,3H,4H,5H-[1,4]diazepino[1,7-a]indol-9-yl]-1,2-dihydropyridin-2-one as free base. MS (EI) 462.2 $[M+H]^+$.

(b) Synthesis of the Hydrochloride Salt

To a solution of 0.025 g (0.054 mmol) of 4-(benzyloxy)-1-[1-chloro-3-(propan-2-yl)-1H,2H,3H,4H,5H-[1,4]diazepino[1,7-a]indol-9-yl]-1,2-dihydropyridin-2-one free base [Example 27, step (a)] in 5 ml of dichloromethane 1 ml of 20% hydrogen chloride in ethyl acetate was added, then the reaction mixture was concentrated. The residue was triturated with diethyl ether, the solid product was filtered, washed with diethyl ether and dried to yield 0.025 g (77%) of the title compound. MS (EI) 462.2 $[M+H]^+$. $^1H$ NMR (400 MHz, DMSO-$d_6$) δ: 10.74-10.88 (br m, 1H), 7.68 (br d, J=8.7 Hz, 1H), 7.58 (d, J=7.6 Hz, 1H), 7.34-7.50 (m, 6H), 7.18 (br d, J=8.8 Hz, 1H), 6.10 (dd, J=7.6, 2.7 Hz, 1H), 5.97 (d, J=2.7 Hz, 1H), 5.15 (s, 2H), 4.90-5.02 (br m, 1H), 4.58-4.71 (br m, 1H), 3.68-3.82 (br m, 3H), 3.25-3.60 (br m, 3H), 3.06-3.21 (br m, 1H), 1.21-1.36 (br m, 6H).

Example 28

4-[(5-chloropyridin-2-yl)methoxy]-1-[3-(cyclopropylmethyl)-1H,2H,3H,4H,5H-[1,4]diazepino[1,7-a]indol-9-yl]-1,2-dihydropyridin-2-ond maleic acid salt (a) Synthesis of the Free Base A mixture of 0.060 g (0.14 mmol) of 4-[(5-chloropyridin-2-yl)methoxy]-1-{1H,2H,3H,4H,5H-[1,4]diazepino[1,7-a]indol-9-yl}-1,2-dihydropyridin-2-one [Example 4, step (b)], 4 ml of methanol, 0.017 ml (0.3 mmol) of acetic acid, 0.112 ml (1.49 mmol) of cyclopropanecarboxaldehyde and 0.127 g (2.02 mmol) of sodium cyanoborohydride was stirred in a closed reaction vessel at 70° C. for 70 min. 6 ml of saturated aqueous $NaHCO_3$ solution was added and the reaction mixture was extracted with 2×15 ml of dichloromethane, the combined organic phases were dried over anhydrous $Na_2SO_4$, filtered and concentrated in vacuum. The crude product was purified by flash column chromatography using Kieselgel 60 (0.040-0.063 mm) as adsorbent (Merck) and a 98:2:1 mixture of dichloromethane, methanol and cc$NH_4OH$ as eluent to yield 0.061 g (91%) of 4-[(5-chloropyridin-2-yl)methoxy]-1-[3-(cyclopropylmethyl)-1H,2H,3H,4H,5H-[1,4]diazepino[1,7-a]indol-9-yl]-1,2-dihydropyridin-2-one as free base. MS (EI) 475.2 $[M+H]^+$.

(b) Synthesis of the Maleic Acid Salt

To a solution of 0.061 g (0.128 mmol) of 4-[(5-chloropyridin-2-yl)methoxy]-1-[3-(cyclopropylmethyl)-1H,2H,3H,4H,5H-[1,4]diazepino[1,7-a]indol-9-yl]-1,2-di hydropyridin-2-one [Example 28, step (a)] in 10 ml of a 9:1 mixture of dichloromethane and ethanol 0.015 g (0.128 mmol) of maleic acid was added, then the dichloromethane was evaporated in vacuum. The residue was triturated with diethyl ether, the solid product was filtered, washed with diethyl ether and dried to yield 0.059 g (77%) of the title compound. MS (EI) 475.2 $[M+H]^+$. $^1H$ NMR (400 MHz, DMSO-$d_6$) δ: 9.50-10.40 (br m, 0.6H), 8.67 (br d, J=2.4 Hz, 1H), 8.03 (dd, J=8.4, 2.5 Hz, 1H), 7.52-7.64 (m, 3H), 7.44 (d, J=2.2 Hz, 1H), 7.05 (dd, J=8.7, 2.1 Hz, 1H), 6.43 (s, 1H), 6.12 (dd, J=7.6, 2.7 Hz, 1H), 6.04 (s, 1.9H), 5.94 (d, J=2.7 Hz, 1H), 5.22 (s, 2H), 4.20-5.10 (br m, 2H), 2.95-4.10 (br m, 8H), 1.05-1.18 (br m, 1H), 0.63-0.72 (br m, 2H), 0.34-0.42 (br m, 2H).

Example 29

4-(benzyloxy)-1-{3-cyclopropyl-1H,2H,3H,4H,5H-[1,4]diazepino[1,7-a]indol-9-yl}-1,2-dihydropyridin-2-one maleic acid salt (a) Synthesis of the Free Base A mixture of 0.1 g (0.26 mmol) of 4-(benzyloxy)-1-{1H,2H,3H,4H,5H-[1,4]diazepino[1,7-a]indol-9-yl}-1,2-dihydropyridin-2-one [Example 3, step (b)], 7 ml of methanol, 0.030 ml (0.52 mmol) of acetic acid, 0.52 ml (2.6 mmol) of (1-ethoxycyclopropoxy)trimethylsilane and 0.22 g (3.5 mmol) of sodium cyanoborohydride was stirred in a closed reaction vessel at 70° C. overnight. 7 ml of methanol was added to the concentrated reaction mixture and it was stirred at 70° C. for 10 min. After cooling to room temperature 15 ml of saturated aqueous $NaHCO_3$ solution was added and the reaction mixture was extracted with 3×20 ml of dichloromethane, the combined organic phases were washed with 10 ml of water and 15 ml of brine, dried over anhydrous $Na_2SO_4$, filtered and concentrated in vacuum. The residue was triturated with 5 ml of a 3:1 mixture of ethanol and diethyl ether, the solid product was filtered, washed with diethyl ether and dried. The crude product was purified by flash column chromatography using Kieselgel 60 (0.040-0.063 mm) as adsorbent (Merck) and a 98:2:1 mixture of dichloromethane, methanol and $ccNH_4OH$ as eluent to yield 0.062 g (55%) of 4-(benzyloxy)-1-{3-cyclopropyl-1H,2H,3H,4H,5H-[1,4]diazepino[1,7-a]indol-9-yl}-1,2-dihydropyridin-2-one as free base. MS (EI) 426.2 $[M+H]^+$.

(b) Synthesis of the Maleic Acid Salt

To a solution of 0.062 g (0.145 mmol) of 4-(benzyloxy)-1-{3-cyclopropyl-1H,2H,3H,4H,5H-[1,4]diazepino[1,7-a]indol-9-yl}-1,2-dihydropyridin-2-one [Example 29, step (a)] in 10 ml of a 9:1 mixture of dichloromethane and ethanol 0.017 g (0.146 mmol) of maleic acid was added, then the dichloromethane was evaporated in vacuum. The residue was triturated with diethyl ether, the solid product was filtered, washed with diethyl ether and dried to yield 0.057 g (72%) of the title compound. MS (EI) 426.2 $[M+H]^+$. $^1H$ NMR (400 MHz, DMSO-$d_6$) δ: 7.34-7.56 (m, 8H), 7.02 (dd, J=8.7, 2.0 Hz, 1H), 6.36 (s, 1H), 6.15 (s, 2H), 6.07 (dd, J=7.6, 2.7 Hz, 1H), 5.95 (d, J=2.7 Hz, 1H), 5.14 (s, 2H), 4.35-4.55 (br m, 2H), 2.90-3.80 (br m, 6H), 2.36-2.58 (br m, 1H), 0.62-0.82 (br m, 4H).

Example 30

4-[(5-chloropyridin-2-yl)methoxy]-1-{3-cyclopropyl-1H,2H,3H,4H,5H-[1,4]diazepino[1,7-a]indol-9-yl}-1,2-dihydropyridin-2-one maleic acid salt (a) Synthesis of the Free Base A mixture of 0.3 g (0.71 mmol) of 4-[(5-chloropyridin-2-yl)methoxy]-1-{1H,2H,3H,4H,5H-[1,4]diazepino[1,7-a]indol-9-yl}-1,2-dihydropyridin-2-one [Example 4, step (b)], 30 ml of methanol, 0.41 ml (7.16 mmol) of acetic acid, 1 g of powdered 4 Å molecular sieves, 0.43 ml (0.21 mmol) of (1-ethoxycyclopropoxy)trimethylsilane and 0.12 g (1.92 mmol) of sodium cyanoborohydride was stirred at reflux temperature for 4 h. The reaction mixture was filtered, the solid material was washed with methanol and the filtrate was concentrated in vacuum. The residue was purified by column chromatography using Kieselgel 60 (0.040-0.063 mm) as adsorbent (Merck) and a 9:1 mixture of dichloromethane and methanol as eluent. The so obtained residue was triturated with ethanol, filtered, washed to with ethanol and dried. The obtained solid product was further purified by column chromatography using Kieselgel 60 (0.040-0.063 mm) as adsorbent (Merck) and a 95:5 mixture of dichloromethane and methanol as eluent, then again purified by column chromatography using a 98:2 mixture of dichloromethane and methanol as eluent. The residue was triturated with diethyl ether, then the diethyl ether was evaporated to yield 0.041 g (12.5%) of 4-[(5-chloropyridin-2-yl)methoxy]-1-{3-cyclopropyl-1H,2H,3H,4H,5H-[1,4]diazepino[1,7-a]indol-9-yl}-1,2-dihydropyridin-2-one as free base. MS (EI) 461.2 $[M+H]^+$.

(b) Synthesis of the Maleic Acid Salt

To a solution of 0.018 g (0.039 mmol) of 4-[(5-chloropyridin-2-yl)methoxy]-1-{3-cyclopropyl-1H,2H,3H,4H,5H-[1,4]diazepino[1,7-a]indol-9-yl}-1,2-dihydropyridin-2-one free base [Example 30, step (a)] in 3 ml of dichloromethane and 1 ml of acetone 0.0046 g (0.040 mmol) of maleic acid was added, then the reaction mixture was concentrated in vacuum. Acetone was added to the residue and the mixture was concentrated to a final volume of 1.0 ml. The solid product separated from acetone, it was filtered, washed with acetone and dried to yield 0.008 g (35%) of the title compound. Concentration of the mother liquid resulted in further 0.005 g (21%) of the title compound. The two fractions were combined. MS (EI) 461.2 $[M+H]^+$. $^1H$ NMR (400 MHz, DMSO-$d_6$) δ: 8.67 (dd, J=2.5, 0.7 Hz, 1H), 8.03 (dd, J=8.4, 2.5 Hz, 1H), 7.50-7.63 (m, 3H), 7.40 (d, J=1.9 Hz, 1H), 7.02 (br d, J=9.0 Hz, 1H), 6.37 (br s, 1H), 6.17 (s, 2.8H), 6.11 (dd, J=7.5, 2.7 Hz, 1H), 5.94 (d, J=2.7 Hz, 1H), 5.22 (s, 2H), 4.28-4.62 (br m, 2H), 2.40-3.80 (br m, 7H), 1.20-1.33 (br m, 1H), 0.62-0.83 (br m, 3H).

Example 31

4-[(5-chloropyridin-2-yl)methoxy]-1-(3-cyclobutyl-1H,2H,3H,4H,5H-[1,4]diazepino[1,7-a]indol-9-yl)-1,2-dihydropyridin-2-one maleic acid salt (a) Synthesis of the Free Base To a mixture of 0.3 g (0.71 mmol) of 4-[(5-chloropyridin-2-yl)methoxy]-1-{1H,2H,3H,4H,5H-[1,4]diazepino[1,7-a]indol-9-yl}-1,2-dihydropyridin-2-one [Example 4, step (b)], 50 ml of dichloromethane, 0.2 ml (1.43 mmol) of triethylamine and 0.07 ml (0.93 mmol) of cyclobutanone 0.23 g (1.09 mmol) of sodium triacetoxyborohydride was added below 10° C. and the reaction mixture was stirred at room temperature overnight. 0.2 ml (1.43 mmol) of triethylamine and 0.12 g (0.57 mmol) of sodium triacetoxyborohydride were added and the mixture was stirred for 24 h. The reaction mixture was washed with 40 ml of 5% aqueous $NaHCO_3$ solution and 2×40 ml of water, the organic phase was dried over anhydrous $Na_2SO_4$, filtered and concentrated in vacuum. The residue was triturated with ethanol, the solid product was filtered, washed with ethanol and dried. The crude product was purified by column chromatography using Kieselgel 60 (0.040-0.063 mm) as adsorbent (Merck) and a 9:1 mixture of dichloromethane and methanol as eluent. The so obtained residue was triturated with ethanol, filtered, washed with ethanol and diethyl ether and dried to yield 0.10 g (300/%) of 4-[(5-chloropyridin-2-yl)methoxy]-1-{3-cyclobutyl-1H,2H,3H,4H,5H-[1,4]diazepino[1,7-a]indol-9-yl}-1,2-dihydropyridin-2-one as free base. MS (EI) 475.2 $[M+H]^+$.

(b) Synthesis of the Maleic Acid Salt

To a solution of 0.060 g (0.126 mmol) of 4-[(5-chloropyridin-2-yl)methoxy]-1-{3-cyclobutyl-1H,2H,3H,4H,5H-[1,4]diazepino[1,7-a]indol-9-yl}-1,2-dihydropyridin-2-one free base [Example 31, step (a)] in 8 ml of dichloromethane and 2 ml of acetone 0.015 g (0.13 mmol) of maleic acid was added, then the reaction mixture was concentrated in vacuum. Acetone was added to the residue and the mixture was concentrated to a final volume of 0.5 ml. The solid product separated from acetone, it was filtered, washed with acetone and dried to yield 0.055 g (74%) of the title compound. MS (EI) 475.2 [M+H]$^+$. $^1$H NMR (400 MHz, DMSO-d$_6$) δ: 9.40-10.40 (br m, 0.7H), 8.67 (d, J=2.5 Hz, 1H), 8.03 (dd, J=8.4, 2.5 Hz, 1H), 7.50-7.63 (m, 3H), 7.43 (d, J=2.0 Hz, 1H), 7.05 (dd, J=8.7, 2.1 Hz, 1H), 6.43 (s, 1H), 6.12 (dd, J=7.6, 2.7 Hz, 1H), 6.06 (s, 2H), 5.94 (d, J=2.7 Hz, 1H), 5.22 (s, 2H), 4.15-5.00 (br m, 2H), 2.70-3.90 (br m, 7H), 2.12-2.31 (br m, 4H), 1.61-1.83 (br m, 2H).

Example 32

4-[(5-chloropyridin-2-yl)methoxy]-1-[3-(2-fluoro-ethyl)-1H,2H,3H,4H,5H-[1,4]diazepino[1,7-a]indol-9-yl]-1,2-dihydropyridin-2-one maleic acid salt (a) Synthesis of the Free Base A mixture of 0.060 g (0.143 mmol) of 4-[(5-chloropyridin-2-yl)methoxy]-1-{1H,2H,3H,4H,5H-[1,4]diazepino[1,7-a]indol-9-yl}-1,2-dihydropyridin-2-one [Example 4, step (b)], 6 ml of acetonitrile, 0.041 g (0.3 mmol) of potassium carbonate, 0.25 g (1.5 mmol) of potassium iodide and 0.112 ml (1.5 mmol) of 1-bromo-2-fluoro-ethane was stirred in a closed reaction vessel at 65° C. overnight, at 50° C. for 72 h, then at 70° C. for 48 h. 10 ml of saturated aqueous NaHCO$_3$ solution was added to the reaction mixture and it was extracted with 3×15 ml of dichloromethane, the combined organic phases were washed with water and brine, dried over anhydrous Na$_2$SO$_4$, filtered and concentrated in vacuum to yield 0.059 g (85%) of 4-[(5-chloropyridin-2-yl)methoxy]-1-[3-(2-fluoro-ethyl)-1H,2H,3H,4H,5H-[1,4]diazepino[1,7-a]indol-9-yl]-1,2-dihydropyridin-2-one as free base. MS (EI) 467.1 [M+H]$^+$.

(b) Synthesis of the Maleic Acid Salt

To a solution of 0.056 g (0.12 mmol) of 4-[(5-chloropyridin-2-yl)methoxy]-1-[3-(2-fluoroethyl)-1H,2H,3H,4H,5H-[1,4]diazepino[1,7-a]indol-9-yl]-1,2-dihydropyridin-2-one free base [Example 32, step (a)] in 2.5 ml of a 9:1 mixture of dichloromethane and ethanol 0.014 g (0.12 mmol) of maleic acid and 0.7 ml of ethanol were added, then the dichloromethane was evaporated in vacuum. The precipitated solid product was filtered, washed with ethanol and diethyl ether and dried to yield 0.052 g (74%) of the title compound. MS (EI) 467.2 [M+H]f. $^1$H NMR (400 MHz, DMSO-d$_6$) δ: 8.67 (d, J=2.4, 0.5 Hz, 1H), 8.03 (dd, J=8.3, 2.4 Hz, 1H), 7.51-7.643 (m, 3H), 7.40 (d, J=2.2 Hz, 1H), 7.02 (dd, J=8.7, 2.1 Hz, 1H), 6.37 (br s, 1H), 6.13 (s, 2H), 6.11 (dd, J=7.7, 2.8 Hz, 1H), 5.94 (d, J=2.7 Hz, 1H), 5.22 (s, 2H), 4.77 (br d, J=47.6 Hz, 2H), 4.30-4.62 (br m, 2H), 2.80-3.90 (br m, 8H).

Example 33

1-[11-chloro-3-(2-fluoroethyl)-1H,2H,3H,4H,5H-[1,4]diazepino[1,7-a]indol-9-yl]-4-[(5-chloropyridin-2-yl)methoxy]-1,2-dihydropyridin-2-one dihydrochloride salt (a) Synthesis of the Free Base To a solution of 0.060 g (0.128 mmol) of 4-[(5-chloropyridin-2-yl)methoxy]-1-[3-(2-fluoroethyl)-1H,2H,3H,4H,5H-[1,4]diazepino[1,7-a]indol-9-yl]-1,2-dihydropyridin-2-one [Example 32, step (a)] in 2 ml of dichloromethane 0.018 g (0.138 mmol) of N-chlorosuccinimide was added and the reaction mixture was stirred at room temperature for 65 min. 20 ml of dichloromethane and 5 ml of 1N aqueous NaOH solution were added to the reaction mixture. The mixture was stirred at room temperature for 1 h, then the phases were separated. The organic phase was washed with 2×5 ml of 1N aqueous NaOH solution, water and brine, then dried over anhydrous Na$_2$SO$_4$, filtered and concentrated in vacuum. The residue was purified by flash column chromatography using Kieselgel 60 (0.040-0.063 mm) as adsorbent (Merck) and a 98:2 mixture of dichloromethane and methanol as eluent to yield 0.022 g (34%) of 1-[11-chloro-3-(2-fluoro-ethyl)-1H,2H,3H,4H,5H-[1,4]diazepino[1,7-a]indol-9-yl]-4-[(5-chloropyridin-2-yl)methoxy]-1,2-dihydropyridin-2-one as free base. MS (EI) 501.1 [M+H]$^+$.

(b) Synthesis of the Dihydrochloride Salt

To a solution of 0.022 g (0.044 mmol) of 1-[11-chloro-3-(2-fluoroethyl)-1H,2H,3H,4H,5H-[1,4]diazepino[1,7-a]indol-9-yl]-4-[(5-chloropyridin-2-yl)methoxy]-1,2-dihydropyridin-2-one [Example 33, step (a)] in 5 ml of dichloromethane 1 ml of 200/% hydrogen chloride in ethyl acetate was added, then the reaction mixture was concentrated. The residue was triturated with diethyl ether, the solid product was filtered, washed with diethyl ether and dried to yield 0.022 g (88%) of the title compound. MS (EI) 501.1 [M+H]$^+$. $^1$H NMR (400 MHz, DMSO-d$_6$) δ: 11.48-11.64 (br m, 1H), 8.68 (dd, J=2.5, 0.6 Hz, 1H), 8.03 (dd, J=8.4, 2.5 Hz, 1H), 7.70 (d, J=9.0 Hz, 1H), 7.58-7.64 (m, 2H), 7.40 (d, J=2.2 Hz, 1H), 7.19 (dd, J=8.7, 2.1 Hz, 1H), 6.14 (dd, J=7.5, 2.8 Hz, 1H), 5.96 (d, J=2.7 Hz, 1H), 5.23 (s, 2H), 4.86-5.05 (br m, 3H), 4.55-4.69 (br m, 1H), 3.75-4.05 (br m, 3H, the signal of HCl overlapped by the signal of H$_2$O), 3.58-3.74 (br m, 2H), 3.22-3.52 (br m, 4H).

Example 34

4-[(5-chloropyridin-2-yl)methoxy]-1-[11-methyl-3-(propan-2-yl)-1H,2H,3H,4H,5H-[1,4]diazepino[1,7-a]indol-9-yl]-1,2-dihydropyridin-2-one maleic acid salt (a) Synthesis of the Free Base A mixture of 1.26 g (2.13 mmol) of 4-[(5-chloropyridin-2-yl)methoxy]-1-[11-iodo-3-(propan-2-yl)-1H,2H,3H,4H,5H-[1,4]diazepino[1,7-a]indol-9-yl]-1,2-di hydropyridin-2-one [Example 26, step (a)], 44 ml of tetrahydrofuran, 0.162 g (0.14 mmol) of tetrakis(triphenylphosphine)palladium(0) and 8 ml (16 mmol) of 2M trimethylaluminum solution in toluene was refluxed for 170 min. The reaction mixture was cooled to room temperature, 150 ml of ethyl acetate, 50 ml of saturated aqueous ammonium chloride solution and 25 ml of brine were added. The phases were separated and the water phase was extracted with 2×50 ml of ethyl acetate. The combined organic phases were washed with 2×50 ml of brine, then dried over anhydrous Na$_2$SO$_4$, filtered and concentrated in vacuum. The residue was triturated with diethyl ether, the solid product was filtered, washed with diethyl ether and dried to yield 0.87 g of crude product. To a solution of 0.568 g of crude product in 25 ml of dichloromethane 0.054 g (0.24 mmol) of N-iodosuccinimide was added at 0° C. and the mixture was stirred at 0° C. for 30 min, then at room temperature for 30 min. 0.027 g (0.12 mmol) of N-iodosuccinimide was added, then after stirring at room temperature for 50 min further 0.027 g (0.12 mmol) of N-iodosuccinimide was added and the reaction mixture was stirred at room temperature for 2 h, then it was kept at 8° C.

for 3 days. 100 ml of dichloromethane was added and the reaction mixture was washed with 2×45 ml of 1N aqueous NaOH solution, 1×45 ml of brine, then dried over anhydrous $Na_2SO_4$, filtered and concentrated in vacuum. The residue was purified by flash column chromatography using Kieselgel 60 (0.040-0.063 mm) as adsorbent (Merck) and a 95:5 mixture of dichloromethane and methanol as eluent. The concentrated fractions (0.159 g) were dissolved in 1.5 ml of ethanol, then the solid product precipitated at room temperature was filtered, washed with ethanol, and a 2:1 mixture of diethyl ether and hexane and dried to yield 0.126 g (18%) of 4-[(5-chloropyridin-2-yl)methoxy]-1-[11-methyl-3-(propan-2-yl)-1H,2H,3H,4H,5H-[1,4]diazepino[1,7-a]indol-9-yl]-1,2-dihydropyridin-2-one as free base. MS (EI) 477.2 $[M+H]^+$.

(b) Synthesis of the Maleic Acid Salt

To a solution of 0.108 g (0.23 mmol) of 4-[(5-chloropyridin-2-yl)methoxy]-1-[11-methyl-3-(propan-2-yl)-1H,2H,3H,4H,5H-[1,4]diazepino[1,7-a]indol-9-yl]-1,2-dihydropyridin-2-one free base [Example 34, step (a)] in 10 ml of a 9:1 mixture of dichloromethane and acetone 0.0271 g (0.23 mmol) of maleic acid was added, then the reaction mixture was concentrated in vacuum. Ethanol was added to the residue and the mixture was concentrated to a final volume of 0.5 ml. Diethyl ether was added and the mixture was concentrated in vacuum. The residue was triturated with diethyl ether, the solid product was filtered, washed with diethyl ether and dried to yield 0.119 g (87%) of the title compound. MS (EI) 477.2 $[M+H]^+$. $^1H$ NMR (400 MHz, DMSO-$d_6$) δ: 9.10-9.90 (m, 0.6H), 8.68 (dd, J=2.5, 0.6 Hz, 1H), 8.03 (dd, J=8.4, 2.5 Hz, 1H), 7.48-7.64 (m, 3H), 7.40 (d, J=2.0 Hz, 1H), 7.04 (dd, J=8.7, 2.1 Hz, 1H), 6.12 (dd, J=7.6, 2.7 Hz, 1H), 6.03 (s, 1.9H), 5.93 (d, J=2.7 Hz, 1H), 5.23 (s, 2H), 4.15-5.05 (br m, 2H), 2.80-3.95 (br m, 7H), 2.21 (s, 3H), 1.24 (br d, J=5.7 Hz, 6H).

Evaluation of MCHR1 Antagonism in Functional Assay

In vitro activity data of selected compounds of the present invention—shown in Table 1—were determined by the following method.

Materials Used:
Cells: human MCH1 (SLC1) AequoScreen® Cell Line (Perkin Elmer ES-370-A, lot No: M4W-A2)
F12 medium (Gibco 21765)
FBS (Gibco 10500)
Antibiotic Antimycotic Solution (Sigma A5955)
G418 (Gibco 11811-023)
Zeocin (Life Technologies R250-01)
96-well plate (Costar 3595)
FLIPR Calcium 5 (no-wash) kit (Molecular Devices R8186)
Probenecid (Sigma P8761)
MCH (Bachem H-1482)

MCH was dissolved in MilliQ water (1 mM), aliquots were taken from the stock solution, and were kept at −20° C. One aliquot was used only once.
HEPES—buffered salt solution (HBSS): 140 mM NaCl, 5 mM KCl, 10 mM HEPES, 2 mM $CaCl_2$, 2 mM $MgCl_2$, 20 mM glucose, pH=7.4, 305-315 mOsm
Assay buffer: HBSS+2 mM probenecid, pH=7.4
Measuring of Cytoplasmic Calcium Concentration ($[Ca^{2+}]_i$):

Cells (human MCH1 (SLC1) AequoScreen® Cell Line, Perkin Elmer ES-370-A, lot No: M4W-A2) expressing human MCH1 receptor, Aequorint and $G_{\alpha 16}$ were cultured in F12 medium (Gibco 21765) containing 10% FBS (Gibco 10500), 1× Antibiotic Antimycotic Solution (Sigma A5955), 400 µg/ml G418 (Gibco 11811-023) and 250 µg/ml zeocin (Life Technologies R250-01).

One day before the $[Ca^{2+}]_i$ measurement cells were plated in a 96-well plate (96-well plate, Costar 3595) at a density of 30000 cells/well in the above described culturing medium, but without G418 and zeocin. On the day of measurement the culture medium was removed from the cells and a fluorescent $Ca^{2+}$-sensitive dye (FLIPR Calcium 5 kit, Molecular Devices R8186) was added to the cells at a 4× dilution compared to the recommended dilution by the manufacturer, in a volume of 100 µl/well, and cells were incubated at 37° C. for 10 min. DMSO stock solutions were made from the test compounds, which were diluted with assay buffer (HEPES buffered salt solution (HBSS): 140 mM NaCl, 5 mM KCl, 10 mM HEPES, 2 mM $CaCl_2$, 2 mM $MgCl_2$, 20 mM glucose, pH=7.4, 305-315 mOsm+2 mM probenecid (Sigma P8761)) (final DMSO concentration was 1%). The vehicle (DMSO, control treatment), or the buffer containing test compounds were added to the cells in a volume of 50 µl/well, and cells were incubated at 37° C. for further 60 min.

$[Ca^{2+}]_i$ measurement was carried out by FlexStation II (Molecular Devices) plate reader fluorimeter (excitation 485 nm, emission 525 nm). MCH was used as agonist (Bachem H-1482). 1 mM stock solution was made from the agonist in distilled water, this solution was distributed into aliquots, which were kept at −20° C. until use. One aliquot was used only once. Fluorescence was detected before addition of MCH for 20 s, and after addition of MCH for 40 s. MCH was applied at an $EC_{80}$ concentration, the $EC_{80}$-values were determined individually for every plate/experiment. For this whole MCH dose-response curves were determined on one part of the plate, 4 parameter sigmoidal curves were fitted to the experimental data by nonlinear regression, MCH $EC_{80}$ values were derived from the fitted curve. The raw fluorescence data were converted into ΔF/F values (the maximum fluorescence value obtained after addition of MCH was normalized to the baseline fluorescence: $\Delta F/F = (F_{max} - F_{baseline})/F_{baseline}$). Inhibitory potency of test compounds was expressed as percent inhibition calculated according to the following formula:

inhibition %=100×(1−(ΔF/$F_{compound}$−ΔF/$F_{DMSO\ buffer}$)/(ΔF/$F_{MCH\ control}$−ΔF/$F_{DMSO\ buffer}$)).

$IC_{50}$ values of the tested compounds were determined by fitting 4 parameter sigmoidal curves to inhibition % data. Data processing, including fitting curves by nonlinear regression, was done by SoftMaxPro software.

$IC_{50}$ Values $IC_{50}$ values of Examples are given in Table 1 below. $IC_{50}$ values of all Examples of the present invention are lower than 50 nM. One third of the compounds have $IC_{50}$ values, determined by the above described method, lower than 10 nM, and $IC_{50}$ values of about one third of the compounds were between 10 nM and 20 nM.

$IC_{50}$ values generated by the above described MCHR1 $[Ca^{2+}]_i$ measurement are given in Table 1 below.

TABLE 1

| Example | MCHR1 $IC_{50}$ (nM) |
| --- | --- |
| 1 | 17.6 |
| 2 | 32.9 |
| 3 | 17.7 |
| 4 | 9.8 |
| 5 | 12 |
| 6 | 11.9 |
| 7 | 27.7 |
| 8 | 123.3 |

TABLE 1-continued

| Example | MCHR1 IC$_{50}$ (nM) |
|---|---|
| 9 | 14.9 |
| 10 | 9.2 |
| 11 | 9.6 |
| 12 | 9 |
| 14 | 7.9 |
| 15 | 6.5 |
| 16 | 7.2 |
| 17 | 18.9 |
| 18 | 15.2 |
| 19 | 8.2 |
| 20 | 6.2 |
| 21 | 8 |
| 22 | 7.2 |
| 23 | 15.7 |
| 24 | 18.5 |
| 25 | 30.7 |
| 26 | 38.8 |
| 27 | 29.9 |
| 28 | 6.2 |
| 29 | 12.9 |
| 30 | 17.2 |
| 31 | 12.3 |
| 32 | 10 |
| 33 | 15.5 |
| 34 | 14.3 |

It is to be understood that the above examples are merely illustrative and do not limit the scope of our invention. The above examples could be modified in numerous respects, and the use of any such modifications or any equivalents is to be considered within the scope of our invention.

The invention claimed is:

1. A compound of the formula (I)

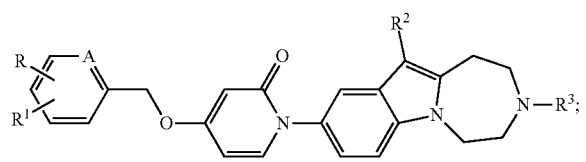

(I)

wherein
A is CH or nitrogen;
R is hydrogen or halogen or $C_1$-$C_6$ straight or branched chain alkyl group;
$R^1$ is hydrogen or halogen, or
  $C_1$-$C_6$ straight or branched chain alkyl group, or
  $C_1$-$C_6$ straight or branched chain alkoxy group, or
  mono- or polyhalogenated $C_1$-$C_6$ straight or branched chain haloalkyl group;
$R^2$ is hydrogen or halogen, or
  $C_1$-$C_6$ straight or branched chain alkyl group, or
  $C_1$-$C_6$ straight or branched chain alkoxy group, or
  mono- or polyhalogenated $C_1$-$C_4$ straight or branched chain haloalkyl group;
$R^3$ is hydrogen, or
  $C_1$-$C_6$ straight or branched chain alkyl group, optionally substituted with $C_3$-$C_6$ cycloalkyl group, or
  mono- or polyhalogenated $C_1$-$C_6$ straight or branched chain haloalkyl group, or
  $C_3$-$C_6$ cycloalkyl group, or
  ($C_1$-$C_6$ straight or branched chain alkyl)-C(O)-group;
or salts, geometric isomers, stereoisomers, diastereomers, or hydrates thereof.

2. The compound of claim 1, wherein $R^3$ is:
hydrogen, or
$C_1$-$C_4$ straight or branched chain alkyl group, optionally substituted with $C_3$-$C_6$ cycloalkyl group, or
$C_3$-$C_6$ cycloalkyl group, or
($C_1$-$C_4$ straight or branched chain alkyl)-C(O)-group.

3. The compound of claim 1, wherein $R^3$ is:
hydrogen, or
$C_1$-$C_4$ straight or branched chain alkyl group, optionally substituted with $C_3$-$C_4$ cycloalkyl group or fluorine, or
$C_3$-$C_4$ cycloalkyl group, or
acetyl.

4. The compound of claim 1, wherein $R^3$ is methyl, ethyl, isopropyl, cyclopropylmethyl, cyclobutyl or fluoroethyl.

5. The compound of claim 1, wherein $R^3$ is isopropyl or cyclopropylmethyl.

6. The compound of claim 1, wherein $R^2$ is hydrogen, halogen, trifluoromethyl, or $C_1$-$C_3$ alkyl group.

7. The compound of claim 1, wherein $R^2$ is hydrogen, fluorine, chlorine, or methyl.

8. The compound of claim 1, wherein $R^2$ is hydrogen.

9. The compound of claim 1, wherein $R^1$ is:
hydrogen or halogen, or
$C_1$-$C_4$ straight or branched chain alkyl group, optionally mono- or polyhalogenated, or
$C_1$-$C_3$ alkoxy group.

10. The compound of claim 1, wherein $R^1$ is hydrogen, fluorine, chlorine, methoxy, or trifluoromethyl.

11. The compound of claim 1, wherein $R^1$ is hydrogen, fluorine, or chlorine.

12. The compound of claim 1, wherein R is hydrogen.

13. The compound of claim 1, wherein R is hydrogen and $R^1$ is chlorine.

14. The compound of claim 1, wherein A is nitrogen.

15. The compound of claim 1, wherein A is CH.

16. The compound of claim 1, selected from the group consisting of:
4-[(5-chloro-pyridin-2-yl)methoxy]-1-{1H,2H,3H,4H,5H-[1,4]diazepino[1,7-a]indol-9-yl}-1,2-dihydropyridin-2-one;
4-[(5-chloro-pyridin-2-yl)methoxy]-1-{3-methyl-1H,2H,3H,4H,5H-[1,4]diazepino[1,7-a]indol-9-yl}-1,2-dihydropyridin-2-one;
4-[(5-chloro-pyridin-2-yl)methoxy]-1-{3-ethyl-1H,2H,3H,4H,5H-[1,4]diazepino[1,7-a]indol-9-yl}-1,2-dihydropyridin-2-one;
4-[(5-fluoro-pyridin-2-yl)methoxy]-1-[3-(propan-2-yl)-1H,2H,3H,4H,5H-[1,4]diazepino[1,7-a]indol-9-yl]-1,2-dihydropyridin-2-one;
4-(benzyloxy)-1-[3-(propan-2-yl)-1H,2H,3H,4H,5H-[1,4]diazepino[1,7-a]indol-9-yl]-1,2-dihydropyridin-2-one;
4-[(5-chloro-pyridin-2-yl)methoxy]-1-[3-(propan-2-yl)-1H,2H,3H,4H,5H-[1,4]diazepino[1,7-a]indol-9-yl]-1,2-dihydropyridin-2-one;
4-[(4-fluoro-phenyl)methoxy]-1-[3-(propan-2-yl)-1H,2H,3H,4H,5H-[1,4]diazepino[1,7-a]indol-9-yl]-1,2-dihydropyridin-2-one;
4-[(4-chloro-phenyl)methoxy]-1-[3-(propan-2-yl)-1H,2H,3H,4H,5H-[1,4]diazepino[1,7-a]indol-9-yl]-1,2-dihydropyridin-2-one;
4-[(2-fluoro-phenyl)methoxy]-1-[3-(propan-2-yl)-1H,2H,3H,4H,5H-[1,4]diazepino[1,7-a]indol-9-yl]-1,2-dihydropyridin-2-one;
1-[11-chloro-3-(propan-2-yl)-1H,2H,3H,4H,5H-[1,4]diazepino[1,7-a]indol-9-yl]-4-[(5-chloro-pyridin-2-yl)methoxy]-1,2-dihydropyridin-2-one;

4-(benzyloxy)-1-[11-chloro-3-(propan-2-yl)-1H,2H,3H,4H,5H-[1,4]diazepino[1,7-a]indol-9-yl]-1,2-dihydropyridin-2-one;

4-[(5-chloro-pyridin-2-yl)methoxy]-1[3-(cyclopropylmethyl)-1H,2H,3H,4H,5H-[1,4]diazepino[1,7-a]indol-9-yl]-1,2-dihydropyridin-2-one;

4-[(5-chloro-pyridin-2-yl)methoxy]-1-{3-cyclopropyl-1H,2H,3H,4H,5H-[1,4]diazepino[1,7-a]indol-9-yl}-1,2-dihydropyridin-2-one;

4-[(5-chloro-pyridin-2-yl)methoxy]-1-{3-cyclobutyl-1H,2H,3H,4H,5H-[1,4]diazepino[1,7-a]indol-9-yl}-1,2-dihydropyridin-2-one;

4-[(5-chloro-pyridin-2-yl)methoxy]-1-[11-methyl-3-(propan-2-yl)-1H,2H,3H,4H,5H-[1,4]diazepino[1,7-a]indol-9-yl]-1,2-dihydropyridin-2-one;

and pharmaceutically acceptable salts thereof.

17. A pharmaceutical composition, comprising a compound of claim 1, and one or more pharmaceutically acceptable excipients, carriers or combination thereof.

18. A method of treating obesity, obesity related comorbid conditions and complications, diabetes, psychiatric diseases accompanied by weight gain, inflammatory bowel diseases, affective dysfunctions, anxiety disorders, or sleep-wake cycle disorders, comprising administering to a subject in need thereof a therapeutically effective amount of a pharmaceutical composition of claim 17.

19. A method of treating obesity, obesity related comorbid conditions and complications, diabetes, psychiatric diseases accompanied by weight gain, inflammatory bowel diseases, affective dysfunctions, anxiety disorders, or sleep-wake cycle disorders, comprising administering to a subject in need thereof a therapeutically effective amount of a compound of claim 1.

20. A compound of formula (II), tert-butyl 9-bromo-1H,2H,3H,4H,5H-[1,4]diazepino[1,7-a]indol-3-carboxylate,

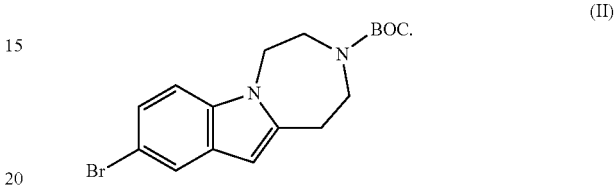

(II)

21. The compound of claim 1, in the form of a pharmaceutically acceptable salt.

* * * * *